(12) United States Patent
Strautmann et al.

(10) Patent No.: US 10,344,381 B2
(45) Date of Patent: Jul. 9, 2019

(54) PROCESS FOR THE GENERATION OF THIN INORGANIC FILMS

(71) Applicant: BASF SE, Ludwigshafen (DE)

(72) Inventors: Julia Strautmann, Bad Laer (DE); Rocco Paciello, Bad Duerkheim (DE); Thomas Schaub, Neustadt (DE); Felix Eickemeyer, Heidelberg (DE); Daniel Loeffler, Birkenheide (DE); Hagen Wilmer, Ludwigshafen (DE); Udo Radius, Kleinrinderfeld (DE); Johannes Berthel, Wuerzburg (DE); Florian Hering, Wuerzburg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/325,840

(22) PCT Filed: Jul. 22, 2015

(86) PCT No.: PCT/EP2015/066747
§ 371 (c)(1),
(2) Date: Jan. 12, 2017

(87) PCT Pub. No.: WO2016/012495
PCT Pub. Date: Jan. 28, 2016

(65) Prior Publication Data
US 2017/0175267 A1 Jun. 22, 2017

(30) Foreign Application Priority Data
Jul. 24, 2014 (EP) .................................. 14178411

(51) Int. Cl.
*C23C 16/455* (2006.01)
*C23C 16/18* (2006.01)
(Continued)

(52) U.S. Cl.
CPC ........ *C23C 16/45553* (2013.01); *C07F 15/04* (2013.01); *C07F 15/06* (2013.01);
(Continued)

(58) Field of Classification Search
CPC .......... C07F 15/04; C07F 15/06; C23C 16/18; C23C 16/45553; C30B 25/08; C30B 25/10
See application file for complete search history.

(56) References Cited

U.S. PATENT DOCUMENTS

2009/0004385 A1  1/2009  Blackwell et al.
2009/0226612 A1  9/2009  Ogawa et al.
(Continued)

FOREIGN PATENT DOCUMENTS

WO   WO 2012/155264 A1   11/2012

OTHER PUBLICATIONS

Schaub et al., Organometallics, 2006, 25, 4196-4206 (Year: 2006).*
(Continued)

*Primary Examiner* — Hua Qi
(74) *Attorney, Agent, or Firm* — Oblon, McClelland, Maier & Neustadt, L.L.P.

(57) ABSTRACT

The present invention is in the field of processes for the generation of thin inorganic films on substrates, in particular atomic layer deposition processes. In detail the present invention relates a process comprising bringing a compound of general formula (I) into the gaseous or aerosol state (Fig.) and depositing the compound of general formula (I) from the gaseous or aerosol state onto a solid substrate, wherein $R^1$ and $R^4$ are independent of each other an alkyl group, an aryl group or a trialkylsilyl group, $R^2$, $R^3$, $R^5$ and $R^6$ are independent of each other hydrogen, an alkyl group, an aryl group or a trialkylsilyl group, n is an integer from 1 to 3, M
(Continued)

is Ni or Co, X is a ligand which coordinates M, and m is an integer from 0 to 4.

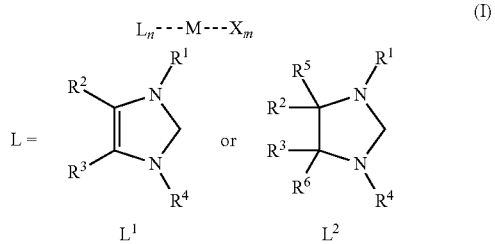

11 Claims, 16 Drawing Sheets

(51) Int. Cl.
  *C07F 15/04* (2006.01)
  *C07F 15/06* (2006.01)
  *C30B 25/10* (2006.01)
  *C30B 25/08* (2006.01)
(52) U.S. Cl.
  CPC .............. *C23C 16/18* (2013.01); *C30B 25/08* (2013.01); *C30B 25/10* (2013.01)

(56) References Cited

U.S. PATENT DOCUMENTS

| | | | |
|---|---|---|---|
| 2009/0305458 A1* | 12/2009 | Hunks | C07C 251/08 438/102 |
| 2011/0120875 A1* | 5/2011 | Norman | C07F 3/003 205/80 |
| 2011/0151615 A1 | 6/2011 | Gordon et al. | |
| 2013/0320344 A1 | 12/2013 | Kim et al. | |
| 2015/0093890 A1 | 4/2015 | Blackwell et al. | |

OTHER PUBLICATIONS

International Search Report dated Oct. 21, 2015, in PCT/EP2015/066747, filed Jul. 22, 2015.
International Preliminary Report on Patentability and Written Opinion dated Jan. 24, 2017 in PCT/EP2015/066747.
Jason P. Coyle, et al., "Deposition of Copper by Plasma-Enhanced Atomic Layer Deposition Using a Novel N-Heterocyclic Carbene Precursor", Chemistry of Materials, vol. 25, 2013, pp. 1132-1138.
Thomas Schaub, et al., "Efficient C—F and C—C Activation by a Novel N-Heterocyclic Carbene—Nickel(0) Complex", Chemistry—A European Journal, vol. 11, 2005, pp. 5024-5030.
Steven M. George, "Atomic Layer Deposition: An Overview", Chemical Reviews, vol. 110, 2010, pp. 111-131.
Thomas Schaub, et al., "Nickel(0) Complexes of N-Alkyl-Substituted N-Heterocyclic Carbenes and Their Use in the Catalytic Carbon-Carbon Bond Activation of Biphenylene", Organometallics, vol. 25, 2006, pp. 4196-4206.
Thomas Schaub, et al., "Efficient nickel mediated carbon-carbon bond cleavage of organonitriles", Dalton Transactions, 2007, pp. 1993-2002.
Peter Fischer, et al., "[Ni(/Pr$_2$Im)$_2$Br$_2$]: A Convenient Entry into NHC Nickel Chemistry", Zeitschrift für Allgemeine and Anorganische Chemie, vol. 638, Issue No. 10, 2012, 1491-1496.
Extended European Search Report dated Nov. 12, 2014 in Patent Application No. 14178411.6.

* cited by examiner

PROCESS FOR THE GENERATION OF THIN INORGANIC FILMS

CROSS-REFERENCE TO RELATED APPLICATIONS

This application is a National Stage of PCT/EP2015/066747, which was filed on Jul. 22, 2015. This application is based upon and claims the benefit of priority to European Application No. 14178411.6, which was filed on Jul. 24, 2014.

BACKGROUND OF THE INVENTION

Field of the Invention

The present invention is in the field of processes for the generation of thin inorganic films on substrates, in particular atomic layer deposition processes.

With the ongoing miniaturization, e.g. in the semiconductor industry, the need for thin inorganic films on substrates increases while the requirements of the quality of such films become stricter. Thin inorganic films serve different purposes such as barrier layers, dielectrica, or separation of fine structures. Several methods for the generation of thin inorganic films are known. One of them is the deposition of film forming compounds from the gaseous state on a substrate. In order to bring metal or semimetal atoms into the gaseous state at moderate temperatures, it is necessary to provide volatile precursors, e.g. by complexation the metals or semimetals with suitable ligands. These ligands need to be removed after deposition of the complexed metals or semimetals onto the substrate.

Description of Related Art

US 2009/0 004 385 A1 discloses N-heterocyclic carbene copper precursors for deposition processes.

T. Schaub et al. disclose in Organometallics volume 25 (2006) page 4196-4206 the preparation of N-heterocylic carbene nickel complexes.

It was an object of the present invention to provide a process for the generation of inorganic films of high quality and reproducibility on solid substrates under economically feasible conditions. It was desired that this process can be performed with as little decomposition of the precursor comprising the metal as possible before it is in contact with the solid substrate. At the same time it was desired to provide a process in which the precursor is easily decomposed after deposited on a solid substrate. It was also aimed at providing a process using metal precursors which can easily be modified and still remain stable in order to fit the precursor's properties to the particular needs.

BRIEF SUMMARY OF THE INVENTION

These objects were achieved by a process comprising bringing a compound of general formula (I) into the gaseous or aerosol state

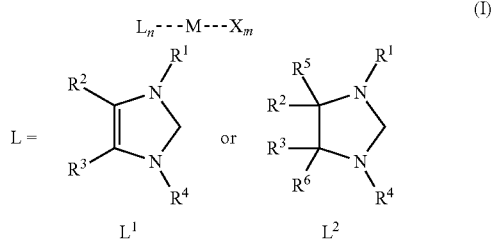

(I)

and depositing the compound of general formula (I) from the gaseous or aerosol state onto a solid substrate, wherein $R^1$ and $R^4$ are independent of each other an alkyl group, an aryl group or a trialkylsilyl group, $R^2$, $R^3$, $R^5$ and $R^6$ are independent of each other hydrogen, an alkyl group, an aryl group or a trialkylsilyl group, n is an integer from 1 to 3, M is Ni or Co, X is a ligand which coordinates M, and m is an integer from 0 to 4.

The present invention further relates to the use of a compound of general formula (I), wherein $R^1$ and $R^4$ are independent of each other an alkyl group, an aryl group or a trialkylsilyl group, $R^2$, $R^3$, $R^5$ and $R^6$ are independent of each other hydrogen, an alkyl group, an aryl group or a trialkylsilyl group, n is an integer from 1 to 3, M is Ni or Co, X is a ligand which coordinates M, and m is an integer from 0 to 4.

for a film formation process on a solid substrate.

Preferred embodiments of the present invention can be found in the description and the claims. Combinations of different embodiments fall within the scope of the present invention.

In the process according to the present invention a compound of general formula (I) is brought into the gaseous or aerosol state. The ligand L is normally bound to the metal M via the carbon atom which is bond to both nitrogen atoms. In general, this carbon atom has no further substituent in addition to the two nitrogen atoms and the metal atom. That is why such compounds are often referred to as carbene compounds. The ligand L can have a double bond in the five-membered ring, referred to as $L^1$, or not, referred to as $L^2$; $L^1$ is preferred.

Figure 1:
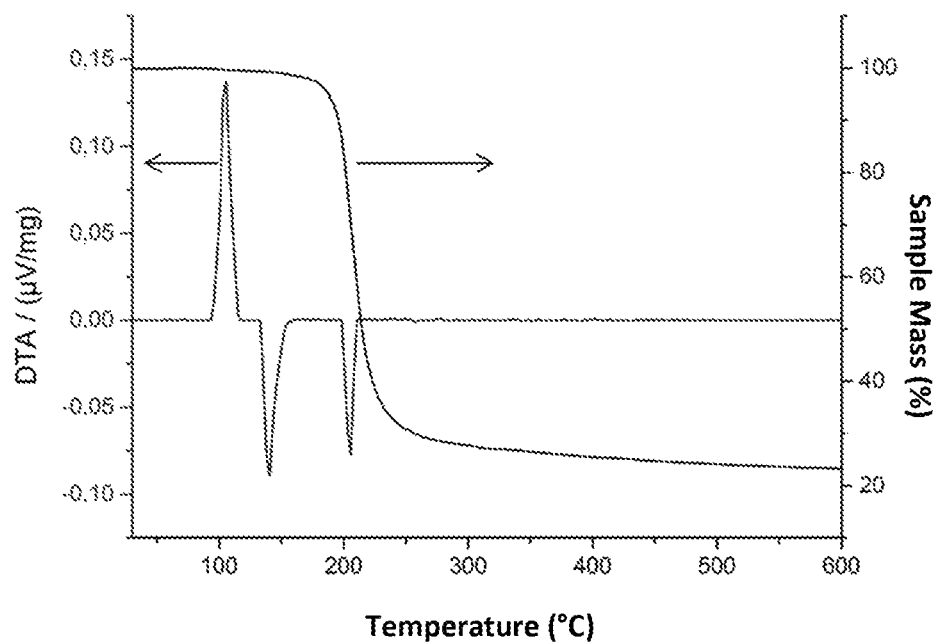
FIG. 1 is a chart showing a differential thermal analysis (DTA) and a thermogravimetry analysis for Compound C1 of Example 1.

DETAILED DESCRIPTION OF THE INVENTION $R^1$ and $R^4$ are independent of each other an alkyl group, an aryl group or a trialkylsilyl group, preferably an alkyl group. $R^1$ and $R^4$ can be the same or different to each other.

$R^2$, $R^3$, $R^5$ and $R^6$ are independent of each other hydrogen, an alkyl group, an aryl group or a trialkylsilyl group. In case of $L^1$ the groups $R^5$ and $R^6$ are absent as obvious from general formula (I). Preferably, all $R^1$, $R^2$, $R^3$, $R^4$, $R^5$ and $R^6$ of the ligand L together contain up to twelve carbon atoms, more preferably up to eight. More preferably $R^2$, $R^3$, $R^5$ and $R^6$ are hydrogen, which means that if L is $L^1$ then $R^2$ and $R^3$ are hydrogen and if L is $L^2$ then $R^2$, $R^3$, $R^5$ and $R^6$ are hydrogen. Also more preferably $R^2$ and $R^3$ are methyl.

An alkyl group can be linear or branched. Examples for a linear alkyl group are methyl, ethyl, n-propyl, n-butyl, n-pentyl, n-hexyl, n-heptyl, n-octyl, n-nonyl, n-decyl. Examples for a branched alkyl group are iso-propyl, iso-butyl, sec-butyl, tert-butyl, 2-methyl-pentyl, 2-ethyl-hexyl, cyclopropyl, cyclohexyl, indanyl, norbornyl. Preferably, the alkyl group is a $C_1$ to $C_8$ alkyl group, more preferably a $C_1$ to $C_6$ alkyl group, in particular a $C_1$ to $C_4$ alkyl group, such as methyl or tert-butyl.

Aryl groups include aromatic hydrocarbons such as phenyl, naphthalyl, anthrancenyl, phenanthrenyl groups and heteroaromatic groups such as pyrryl, furanyl, thienyl, pyridinyl, quinoyl, benzofuryl, benzothiophenyl, thienothienyl. Several of these groups or combinations of these groups are also possible like biphenyl, thiophenyl or furanylthienyl. Aryl groups can be substituted for example by halogens like fluoride, chloride, bromide, iodide; by pseudohalogens like cyanide, cyanate, thiocyanate; by alcohols; alkyl chains or alkoxy chains. Aromatic hydrocarbons are preferred, phenyl is more preferred.

A trialkylsilyl group can bear the same or different alkyl groups. Preferably, the trialkylsilyl group bears $C_1$ to $C_6$ alkyl groups, more preferably $C_1$ to $C_4$ alkyl groups. Examples for a trialkylsilyl group with the same alkyl groups are trimethylsilyl, triethylsilyl, tri-n-propylsilyl, tri-iso-propylsilyl, tricyclohexylsilyl. Examples for a trialkylsilyl group with different alkyl groups are dimethyl-tertbutylsilyl, dimethylcyclohexylsilyl, methyl-di-iso-propylsilyl.

It is preferred that the molecular weight of the compound of general formula (I) is up to 1000 g/mol, more preferred up to 800 g/mol, in particular up to 600 g/mol.

The compound of general formula (I) according to the present invention can contain from 1 to 3 ligands L, i.e. n is an integer from 1 to 3. Preferably, n is from 1 to 2, more preferably n equals 2. If more than one ligand L are present in the compound of general formula (I), they can be all the same or different to each other. It is further possible that both an $L^1$ and an $L^2$ ligand are present in the compound of general formula (I). Preferably, all ligands L in the compound of general formula (I) are the same. M in general formula (I) is Ni or Co, preferably Ni.

According to the present invention the ligand X in the compound of general formula (I) can be any ligand which coordinates M. If X bears a charge, m is normally chosen such that the compound of general formula (I) is neutrally charged. If more than one such ligand is present in the compound of general formula (I), i.e. m>1, they can be the same or different from each other. If m>2, it is possible that two ligands X are the same and the remaining X are different from these. X can be in any ligand sphere of the metal or semimetal M, e.g. in the inner ligand sphere, in the outer ligand sphere, or only loosely associated to M. Preferably, X is in the inner ligand sphere of M. It is believed that if all ligands X are in the inner ligand sphere of M the volatility of the compound of general formula (I) is high such that it can be brought into the gaseous or aerosol state without decomposition.

The ligand X in the compound of general formula (I) according to the present invention includes anions of halogens like fluoride, chloride, bromide or iodide and pseudohalogens like cyanide, isocyanide, cyanate, isocyanate, thiocyanate, isothiocyanate, or azide. Furthermore, X can be any amine ligand in which the coordinating nitrogen atom is either aliphatic like in dialkylamine, piperidine, morpholine, hexamethyldisilazane; amino imides; or aromatic like in pyrrole, indole, pyridine, or pyrazine. The nitrogen atom of the amine ligand is often deprotonated before coordinated to M. Furthermore, X can be an amide ligand such as formamide or acetamide; an amidinate ligand such as acetamidine; or a guanidinate ligand such guanidine. It is also possible that X is a ligand in which an oxygen atom coordinates to the metal or semimetal. Examples are alkanolates, tetrahydrofurane, acetylacetonate, acetyl acetone, or 1,1,1,5,5,5-pentafluoroacetylacetone. Other suitable examples for X include both a nitrogen and an oxygen atom which both coordinate to M including dimethylamino-iso-propanol. Also suitable for X are ligands which coordinate via a phosphorous atom to M. These include trialkyl phosphines such as trimethyl phosphine, tri-tert-butyl phosphine, tricyclohexyl phosphine, or aromatic phosphines such as triphenyl phosphine, or tritolylphosphine.

Further suitable ligands X are alkyl anions like methyl, ethyl, or butyl anions. Another possible ligand X is hydride. X can also be an unsaturated hydrocarbon which coordinates with the π-bond to M. Unsaturated hydrocarbons include olefins like ethylene, propylene, iso-butylene, cyclohexene, cyclooctene, cyclooctadiene, styrene; and alkynes like ethyne, propyne, 2-butyne. X can also be an unsaturated anionic hydrocarbon which can coordinate both via the anion and the unsaturated bond such as allyl or 2-methyl-allyl. Cyclopentadiene anions and substituted cyclopentadiene anions are also suitable for X. Another suitable example for X is carbonmonoxide CO or nitric oxide NO. It is particularly preferred that one X is NO and the other X are CO. It is also possible to use molecules which contain multiple atoms which coordinate to M. Examples are bipyridine, o-terpyridine, ethylenediamine, ethylenedi(bisphenylphosphine).

Small ligands which have a low vaporization temperature are preferred for X. Particularly preferred ligands X are carbonmonoxide, cyanide, bromide, methyl, ethylene, cyclooctene or 2-butyne. Small anionic ligands which can easily be transformed into volatile neutral compounds upon protonation, for example by surface-bound protons, are preferred for X. Examples include methyl, ethyl, propyl, dimethylamide, diethylamide, allyl, 2-methyl-allyl.

Some preferred examples for compounds of general formula (I) are given in the following table.

| No. | L | $R^1$ | $R^2$ | $R^3$ | $R^4$ | $R^5$ | $R^6$ | n | M | X | m |
|---|---|---|---|---|---|---|---|---|---|---|---|
| C1 | $L^1$ | iso-propyl | H | H | iso-propyl | — | — | 2 | Ni | ethylene | 1 |
| C2 | $L^1$ | iso-propyl | H | H | iso-propyl | — | — | 2 | Ni | CO | 2 |
| C3 | $L^1$ | iso-propyl | H | H | iso-propyl | — | — | 2 | Ni | Br | 2 |
| C4 | $L^1$ | methyl | H | H | methyl | — | — | 2 | Ni | CO | 2 |
| C5 | $L^1$ | Dipp | H | H | Dipp | — | — | 1 | Ni | CO | 3 |
| C6 | $L^1$ | tert-butyl | H | H | tert-butyl | — | — | 1 | Ni | CO | 2 |
| C7 | $L^1$ | n-propyl | H | H | n-propyl | — | — | 2 | Ni | CO | 2 |
| C8 | $L^1$ | iso-propyl | H | H | iso-propyl | — | — | 2 | Ni | COE | 1 |
| C9 | $L^1$ | iso-propyl | H | H | iso-propyl | — | — | 2 | Ni | CN | 2 |
| C10 | $L^1$ | iso-propyl | H | H | iso-propyl | — | — | 2 | Ni | methyl | 2 |
| C11 | $L^1$ | iso-propyl | H | H | iso-propyl | — | — | 2 | Ni | styrene | 1 |
| C12 | $L^1$ | iso-propyl | H | H | iso-propyl | — | — | 2 | Ni | 2-butyene | 1 |
| C13 | $L^1$ | methyl | H | H | methyl | — | — | 2 | Ni | 2-butyene | 1 |
| C14 | $L^1$ | methyl | H | H | methyl | — | — | 2 | Ni | COE | 1 |
| C15 | $L^1$ | methyl | H | H | methyl | — | — | 2 | Ni | CN | 2 |
| C16 | $L^1$ | tert-butyl | H | H | tert-butyl | — | — | 1 | Ni | styrene | 2 |
| C17 | $L^1$ | methyl | H | H | methyl | — | — | 2 | Co | NO CO | 2 |
| C18 | $L^1$ | methyl | methyl | methyl | methyl | — | — | 2 | Co | NO CO | 2 |
| C19 | $L^1$ | methyl | H | H | tert-butyl | — | — | 2 | Co | NO CO | 2 |
| C20 | $L^1$ | iso-propyl | H | H | iso-propyl | — | — | 2 | Co | NO CO | 2 |
| C21 | $L^1$ | n-propyl | H | H | n-propyl | — | — | 2 | Co | NO CO | 2 |
| C22 | $L^1$ | iso-propyl | methyl | methyl | iso-propyl | — | — | 2 | Co | NO CO | 2 |
| C23 | $L^1$ | cyclo-hexyl | H | H | cyclo-hexyl | — | — | 2 | Co | NO CO | 2 |

-continued

| No. | L | $R^1$ | $R^2$ | $R^3$ | $R^4$ | $R^5$ | $R^6$ | n | M | X | m |
|---|---|---|---|---|---|---|---|---|---|---|---|
| C24 | $L^1$ | methyl | H | H | methyl | — | — | 1 | Co | NO<br>CO<br>CO | 3 |
| C25 | $L^1$ | methyl | methyl | methyl | methyl | — | — | 1 | Co | NO<br>CO<br>CO | 3 |
| C26 | $L^1$ | methyl | H | H | tert-butyl | — | — | 1 | Co | NO<br>CO<br>CO | 3 |
| C27 | $L^1$ | iso-propyl | H | H | iso-propyl | — | — | 1 | Co | NO<br>CO<br>CO | 3 |
| C28 | $L^1$ | n-propyl | H | H | n-propyl | — | — | 1 | Co | NO<br>CO<br>CO | 3 |
| C29 | $L^1$ | iso-propyl | methly | methyl | iso-propyl | — | — | 1 | Co | NO<br>CO<br>CO | 3 |
| C30 | $L^1$ | mesityl | H | H | mesityl | — | — | 1 | Co | NO<br>CO<br>CO | 3 |
| C31 | $L^1$ | Dipp | H | H | Dipp | — | — | 1 | Co | NO<br>CO<br>CO | 3 |
| C32 | $L^1$ | iso-propyl | H | H | iso-propyl | — | — | 2 | Co | CO | 2 |
| C33 | $L^2$ | methyl | H | H | methyl | H | H | 2 | Co | CO | 2 |
| C34 | $L^1$ | tert-butyl | H | H | tert-butyl | — | — | 2 | Co | CO | 2 |
| C35 | $L^2$ | iso-propyl | H | H | iso-propyl | H | H | 2 | Co | methyl | 2 |
| C36 | $L^1$ | phenyl | H | H | phenyl | — | — | 2 | Ni | CO | 2 |
| C37 | $L^2$ | phenyl | H | H | phenyl | H | H | 2 | Co | CO | 2 |
| C38 | $L^2$ | TMS | H | H | TMS | H | H | 2 | Ni | CO | 2 |
| C39 | $L^1$ | TMS | H | H | TMS | — | — | 2 | Co | CO | 2 |
| C40 | $L^1$ | iso-propyl | H | H | iso-propyl | — | — | 3 | Ni | — | 0 |
| C41 | $L^2$ | methyl | H | H | methyl | H | H | 3 | Co | — | 0 |
| C42 | $L^2$ | phenyl | H | H | phenyl | H | H | 2 | Ni | H | 2 |
| C43 | $L^1$ | iso-propyl | H | H | iso-propyl | — | — | 2 | Co | cp | 2 |
| C44 | $L^2$ | TIPS | H | H | TIPS | H | H | 2 | Ni | allyl | 2 |
| C45 | $L^2$ | methyl | H | H | methyl | H | H | 2 | Co | $CF_3$ | 2 |
| C46 | $L^1$ | methyl | methyl | methyl | methyl | — | — | 2 | Ni | CO | 2 |
| C47 | $L^2$ | phenyl | $CF_3$ | $CF_3$ | phenyl | H | H | 2 | Co | CO | 2 |
| C48 | $L^1$ | iso-propyl | H | H | methyl | — | — | 2 | Ni | CO | 2 |
| C49 | $L^2$ | phenyl | H | H | TMS | H | H | 2 | Co | CN | 2 |
| C50 | $L^1$ | iso-propyl | methyl | H | tert-butyl | — | — | 2 | Co | H | 2 |
| C51 | $L^1$ | iso-propyl | H | H | iso-propyl | — | — | 1 | Ni | CO | 3 |
| C52 | $L^2$ | phenyl | H | H | phenyl | H | H | 1 | Co | CN | 3 |
| C53 | $L^1$ | iso-propyl | H | H | iso-propyl | — | — | 2 | Ni | COH | 2 |
| C54 | $L^2$ | methyl | methyl | methyl | methyl | methyl | methyl | 2 | Co | CO | 2 |
| C55 | $L^1$ | methyl | H | H | methyl | — | — | 1 | Co | CO<br>$PMe_3$<br>NO | 3 |
| C56 | $L^1$ | methyl | H | H | methyl | — | — | 1 | Co | CO<br>$PMe_3$<br>$PMe_3$ | 3 |

Dipp stands for 2,6-di-iso-propylphenyl, COE for cyclooctene, TMS for trimethylsilyl, TIPS for tri-iso-propylsilyl, cp for cyclopentadienyl, $PMe_3$ for trimethylphosphine.

The compound of general formula (I) used in the process according to the present invention is used at high purity to achieve the best results. High purity means that the substance used contains at least 90 wt.-% compound of general formula (I), preferably at least 95 wt.-% compound of general formula (I), more preferably at least 98 wt.-% compound of general formula (I), in particular at least 99 wt.-% compound of general formula (I). The purity can be determined by elemental analysis according to DIN 51721 (Prüfung fester Brennstoffe—Bestimmung des Gehaltes an Kohlenstoff und Wasserstoff—Verfahren nach Radmacher-Hoverath, August 2001).

In the process according to the present invention the compound of general formula (I) is brought into the gaseous or aerosol state. This can be achieved by heating the compound of general formula (I) to elevated temperatures. In any case a temperature below the decomposition temperature of the compound of general formula (I) has to be chosen. Preferably, the heating temperature ranges from slightly above room temperature to 300° C., more preferably from 30° C. to 250° C., even more preferably from 40° C. to 200° C., in particular from 50° C. to 150° C.

Another way of bringing the compound of general formula (I) into the gaseous or aerosol state is direct liquid injection (DLI) as described for example in US 2009/0 226 612 A1. In this method the compound of general formula (I) is typically dissolved in a solvent and sprayed in a carrier gas or vacuum. Depending on the vapor pressure of the compound of general formula (I), the temperature and the pressure the compound of general formula (I) is either brought into the gaseous state or into the aerosol state. Various solvents can be used provided that the compound of general formula (I) shows sufficient solubility in that solvent such as at least 1 g/l, preferably at least 10 g/l, more preferably at least 100 g/l. Examples for these solvents are coordinating solvents such as tetrahydrofuran, dioxane, diethoxyethane, pyridine or non-coordinating solvents such as hexane, heptane, benzene, toluene, or xylene. Solvent mixtures are also suitable. The aerosol comprising the compound of general formula (I) should contain very fine liquid droplets or solid particles. Preferably, the liquid droplets or solid particles have a weight average diameter of not more than 500 nm, more preferably not more than 100 nm. The weight average diameter of liquid droplets or solid particles can be determined by dynamic light scattering as described in ISO 22412:2008. It is also possible that a part of the compound of general formula (I) is in the gaseous state and the rest is in the aerosol state, for example due to a limited vapor pressure of the compound of general formula (I) leading to partial evaporation of the compound of general formula (I) in the aerosol state.

It is preferred to bring the compound of general formula (I) into the gaseous or aerosol state at decreased pressure. In this way, the process can usually be performed at lower heating temperatures leading to decreased decomposition of the compound of general formula (I). It is also possible to use increased pressure to push the compound of general formula (I) in the gaseous or aerosol state towards the solid substrate. Often, an inert gas, such as nitrogen or argon, is used as carrier gas for this purpose. Preferably, the pressure is 10 bar to $10^{-7}$ mbar, more preferably 1 bar to $10^{-3}$ mbar, in particular 1 to 0.01 mbar, such as 0.1 mbar.

In the process according to the present invention a compound of general formula (I) is deposited on a solid substrate from the gaseous or aerosol state. The solid substrate can be any solid material. These include for example metals, semimetals, oxides, nitrides, and polymers. It is also possible that the substrate is a mixture of different materials. Examples for metals are aluminum, steel, zinc, and copper. Examples for semimetals are silicon, germanium, and gallium arsenide. Examples for oxides are silicon dioxide, titanium dioxide, and zinc oxide. Examples for nitrides are silicon nitride, aluminum nitride, titanium nitride, and gallium nitride. Examples for polymers are polyethylene terephthalate (PET), polyethylene naphthalene-dicarboxylic acid (PEN), and polyamides.

The solid substrate can have any shape. These include sheet plates, films, fibers, particles of various sizes, and substrates with trenches or other indentations. The solid substrate can be of any size. If the solid substrate has a particle shape, the size of particles can range from below 100 nm to several centimeters, preferably from 1 μm to 1 mm. In order to avoid particles or fibers to stick to each other while the compound of general formula (I) is deposited onto them, it is preferably to keep them in motion. This can, for example, be achieved by stirring, by rotating drums, or by fluidized bed techniques.

The deposition takes place if the substrate comes in contact with the compound of general formula (I). Generally, the deposition process can be conducted in two different ways: either the substrate is heated above or below the decomposition temperature of the compound of general formula (I). If the substrate is heated above the decomposition temperature of the compound of general formula (I), the compound of general formula (I) continuously decomposes on the surface of the solid substrate as long as more compound of general formula (I) in the gaseous or aerosol state reaches the surface of the solid substrate. This process is typically called chemical vapor deposition (CVD). Usually, an inorganic layer of homogeneous composition, e.g. the metal or semimetal oxide or nitride, is formed on the solid substrate as the organic material is desorbed from the metal or semimetal M. Typically the solid substrate is heated to a temperature in the range of 300 to 1000° C., preferably in the range of 350 to 600° C.

Alternatively, the substrate is below the decomposition temperature of the compound of general formula (I). Typically, the solid substrate is at a temperature equal to or lower than the temperature of the place where the compound of general formula (I) is brought into the gaseous or aerosol state, often at room temperature or only slightly above. Preferably, the temperature of the substrate is at least 30° C. lower than the place where the compound of general formula (I) is brought into the gaseous or aerosol state. Preferably, the temperature of the substrate is from room temperature to 400° C., more preferably from 100 to 300° C., such as 150 to 220° C.

The deposition of compound of general formula (I) onto the solid substrate is either a physisorption or a chemisorption process. Preferably, the compound of general formula (I) is chemisorbed on the solid substrate. One can determine if the compound of general formula (I) chemisorbs to the solid substrate by exposing a quartz microbalance with a quartz crystal having the surface of the substrate in question to the compound of general formula (I) in the gaseous or aerosol state. The mass increase is recorded by the eigen frequency of the quartz crystal. Upon evacuation of the chamber in which the quartz crystal is placed the mass should not decrease to the initial mass, but about a monolayer of the residual compound of general formula (I) remains if chemisorption has taken place. In most cases where chemisorption of the compound of general formula (I) to the solid substrate occurs, the x-ray photoelectron spectroscopy (XPS) signal (ISO 13424 EN—Surface chemical analysis—X-ray photoelectron spectroscopy—Reporting of results of thin-film analysis; October 2013) of M changes due to the bond formation to the substrate.

If the temperature of the substrate in the process according to the present invention is kept below the decomposition temperature of the compound of general formula (I), typically a monolayer is deposited on the solid substrate. Once a molecule of general formula (I) is deposited on the solid substrate further deposition on top of it usually becomes less likely. Thus, the deposition of the compound of general formula (I) on the solid substrate preferably represents a self-limiting process step. The typical layer thickness of a self-limiting deposition processes step is from 0.01 to 1 nm, preferably from 0.02 to 0.5 nm, more preferably from 0.03 to 0.4 nm, in particular from 0.05 to 0.2 nm. The layer thickness is typically measured by ellipsometry as described in PAS 1022 DE (Referenzverfahren zur Bestimmung von optischen and dielektrischen Materialeigenschaften sowie der Schichtdicke dünner Schichten mittels Ellipsometrie; February 2004).

Often it is desired to build up thicker layers than those just described. In order to achieve this in the process according to the present invention it is preferable to decompose the deposited compound of general formula (I) by removal of all L and X after which further compound of general formula (I) is deposited. This sequence is preferably performed at least twice, more preferably at least 10 times, in particular at least 50 times. Removing all L and X in the context of the present invention means that at least 95 wt.-% of the total weight of L and X in the deposited compound of general formula (I) are removed, preferably at least 98 wt.-%, in particular at least 99 wt.-%. The decomposition can be effected in various ways. The temperature of the solid substrate can be increased above the decomposition temperature.

Furthermore, it is possible to expose the deposited compound of general formula (I) to a plasma like an oxygen plasma or a hydrogen plasma; to oxidants like oxygen, oxygen radicals, ozone, nitrous oxide ($N_2O$), nitric oxide (NO), nitrogendioxde ($NO_2$) or hydrogenperoxide; to reducing agents like hydrogen, alcohols, hydroazine or hydroxylamine; or solvents like water. It is preferable to use oxidants, plasma or water to obtain a layer of a metal oxide or a semimetal oxide. Exposure to water, an oxygen plasma or ozone is preferred. Exposure to water is particularly preferred. If layers of elemental metal or semimetal are desired it is preferable to use reducing agents. Preferred examples are hydrogen, hydrogen radicals, hydrogen plasma, ammonia, ammonia radicals, ammonia plasma, hydrazine, N,N-dimethylhydrazine, silane, disilane, trisilane, cyclopentasilane, cyclohexasilane, dimethylsilane, diethylsilane, or trisilylamine; more preferably hydrogen, hydrogen radicals, hydrogen plasma, ammonia, ammonia radicals, ammonia plasma, hydrazine, N,N-dimethylhydrazine, silane; in particular hydrogen. The reducing agent can either directly cause the decomposition of the deposited compound of general formula (I) or it can be applied after the decomposition of the deposited compound of general formula (I) by a different agent, for example water. For layers of metal nitrides it is preferable to use ammonia or hydrazine. Small molecules are believed to easily access the metal or semimetal M due to the planarity of the aromatic part of ligand L which is the consequence of the conjugation of the two iminomethyl groups to the pyrrole unit in ligand L. Typically, a low decomposition time and high purity of the generated film is observed.

A deposition process comprising a self-limiting process step and a subsequent self-limiting reaction is often referred to as atomic layer deposition (ALD). Equivalent expressions are molecular layer deposition (MLD) or atomic layer epitaxy (ALE). Hence, the process according to the present invention is preferably an ALD process. The ALD process is described in detail by George (Chemical Reviews 110 (2010), 111-131).

A particular advantage of the process according to the present invention is that the compound of general formula (I) is very versatile, so the process parameters can be varied in a broad range. Therefore, the process according to the present invention includes both a CVD process as well as an ALD process.

Depending on the number of sequences of the process according to the present invention performed as ALD process, films of various thicknesses are generated. Preferably, the sequence of depositing the compound of general formula (I) onto a solid substrate and decomposing the deposited compound of general formula (I) is performed at least twice. This sequence can be repeated many times, for example 10 to 500, such as 50 or 100 times. Usually, this sequence is not repeated more often than 1000 times. Ideally, the thickness of the film is proportional to the number of sequences performed. However, in practice some deviations from proportionality are observed for the first 30 to 50 sequences. It is assumed that irregularities of the surface structure of the solid substrate cause this non-proportionality.

One sequence of the process according to the present invention can take from milliseconds to several minutes, preferably from 0.1 second to 1 minute, in particular from 1 to 10 seconds. The longer the solid substrate at a temperature below the decomposition temperature of the compound of general formula (I) is exposed to the compound of general formula (I) the more regular films formed with less defects.

The process according to the present invention yields a film. A film can be only one monolayer of deposited compound of formula (I), several consecutively deposited and decomposed layers of the compound of general formula (I), or several different layers wherein at least one layer in the film was generated by using the compound of general formula (I). A film can contain defects like holes. These defects, however, generally constitute less than half of the surface area covered by the film. The film is preferably an inorganic film. In order to generate an inorganic film, all organic ligands L and X have to be removed from the film as described above. More preferably, the film is an elemental metal film. The film can have a thickness of 0.1 nm to 1 µm or above depending on the film formation process as described above. Preferably, the film has a thickness of 0.5 to 50 nm. The film preferably has a very uniform film thickness which means that the film thickness at different places on the substrate varies very little, usually less than 10%, preferably less than 5%. Furthermore, the film is preferably a conformal film on the surface of the substrate. Suitable methods to determine the film thickness and uniformity are XPS or ellipsometry.

The film obtained by the process according to the present invention can be used in an electronic element. Electronic elements can have structural features of various sizes, for example from 100 nm to 100 µm. The process for forming the films for the electronic elements is particularly well suited for very fine structures. Therefore, electronic elements with sizes below 1 µm are preferred. Examples for electronic elements are field-effect transistors (FET), solar cells, light emitting diodes, sensors, or capacitors. In optical devices such as light emitting diodes or light sensors the film according to the present invention serves to increase the reflective index of the layer which reflects light. An example for a sensor is an oxygen sensor, in which the film can serve as oxygen conductor, for example if a metal oxide film is prepared. In field-effect transistors out of metal oxide semiconductor (MOS-FET) the film can act as dielectric layer or as diffusion barrier. It is also possible to make semiconductor layers out of the films in which elemental nickel-silicon is deposited on a solid substrate.

Preferred electronic elements are transistors. Preferably the film acts as contact in a transistor. If the transistor is made of silicon it is possible that after deposition of nickel or cobalt and heating some silicon diffuses into the nickel to form for example NiSi or $CoSi_2$.

Description of the Figures

FIGS. 1 to 30 show differential thermal analysis and the thermogravimetry measurements for the compounds of the examples. The arrows indicate which curve corresponds to which scale.

EXAMPLES

General Procedures

For the differential thermal analysis and the thermogravimetry measurement (DTA/TG) the sample is placed in an alumina crucible and put in an apparatus in which a mixture of nitrogen and argon is passed over the sample at 20 mL/min. The temperature is increased from 25 to 950° C. at 10° C./min.

For the differential scanning calorimetry measurement (DSC) the sample is placed in an alumina crucible and put in an apparatus in which 20 ml nitrogen are passed over the sample per minute. The temperature is increase from 25 to 400° C. at a rate of 10° C./min.

Example 1

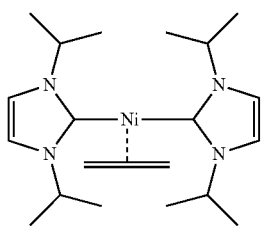

C1

Compound C1 was synthesized and characterized according to T. Schaub et al., Chemistry—A European Journal, volume 11 (2005) pages 5024-5030.

The differential thermal analysis (DTA) and the thermogravimetry analysis of C1 are depicted in FIG. 1. The DTA shows an exothermic peak at 93° C. and two endothermic peaks at 131° C. and 198° C. respectively. Deriving from the thermogravimetry analysis, the sample has lost 80.8% of its mass at 600° C.

Example 2

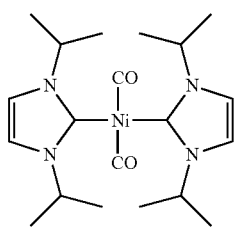

C2

Compound C2 was synthesized and characterized according to T. Schaub et al., Organometallics, volume 25 (2006), pages 4196-4206.

Figure 2:
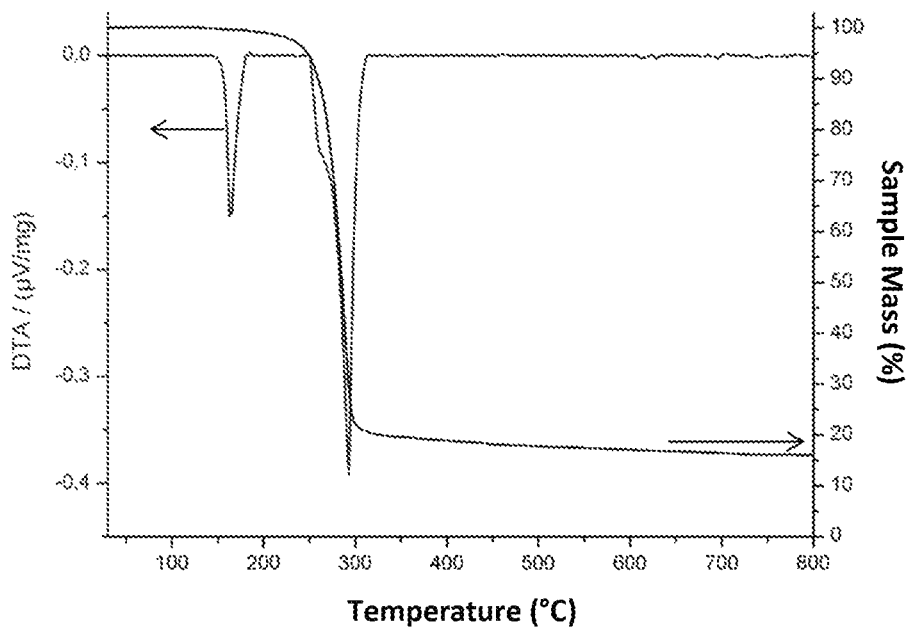
FIG. 2 is a chart showing a differential thermal analysis (DTA) and a thermogravimetry analysis for Compound C2 of Example 2.

The differential thermal analysis and the thermogravimetry analysis of C2 are depicted in FIG. 2. The DTA shows two endothermic peaks at 154° C. and 254° C. respectively. Deriving from the thermogravimetry analysis, the sample has lost 81.8% of its mass at 600° C.

Example 3

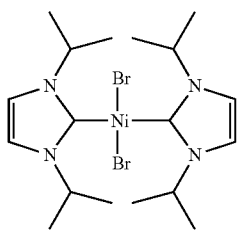

C3

Compound C3 was synthesized and characterized according to P. Fischer et al., Zeitschrift für Allgemeine and Anorganische Chemie, volume 638 (2012), pages 1491-1496.

Figure 3:
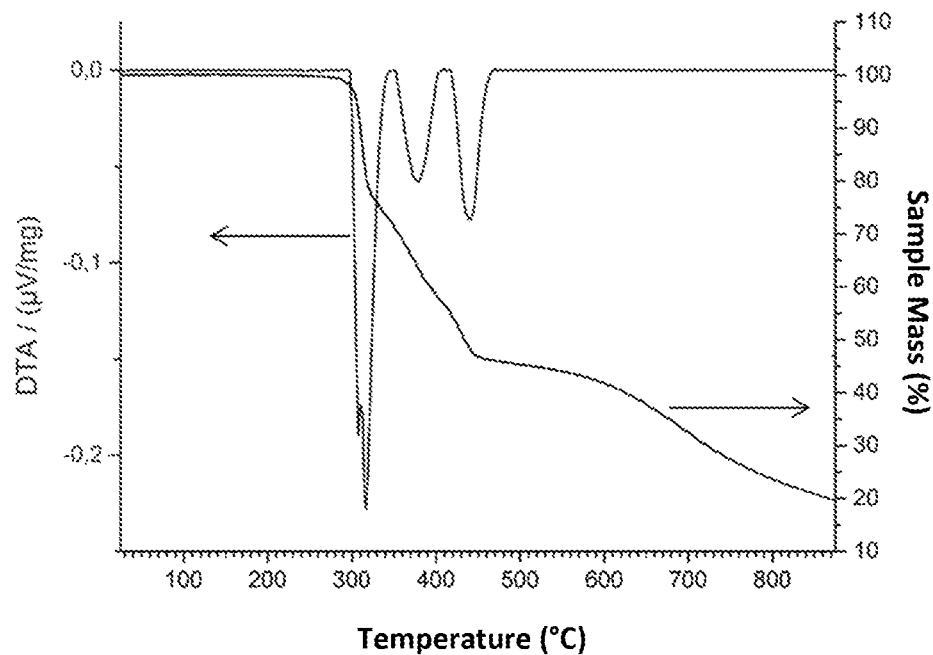
FIG. 3 is a chart showing a differential thermal analysis (DTA) and a thermogravimetry analysis for Compound C3 of Example 3.

The differential thermal analysis and the thermogravimetry analysis of C3 are depicted in FIG. 3. The DTA shows four endothermic peaks at 298° C., 312° C., 355° C. and 420° C. respectively. Deriving from the thermogravimetry analysis, the sample has lost 21.1% of its mass at 300° C. and 31.5% at 420° C.

Example 4

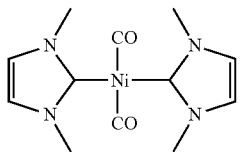

C4

Compound C4 was synthesized and characterized according to T. Schaub et al., Organometallics, volume 25 (2006), pages 4196-4206.

Figure 4:
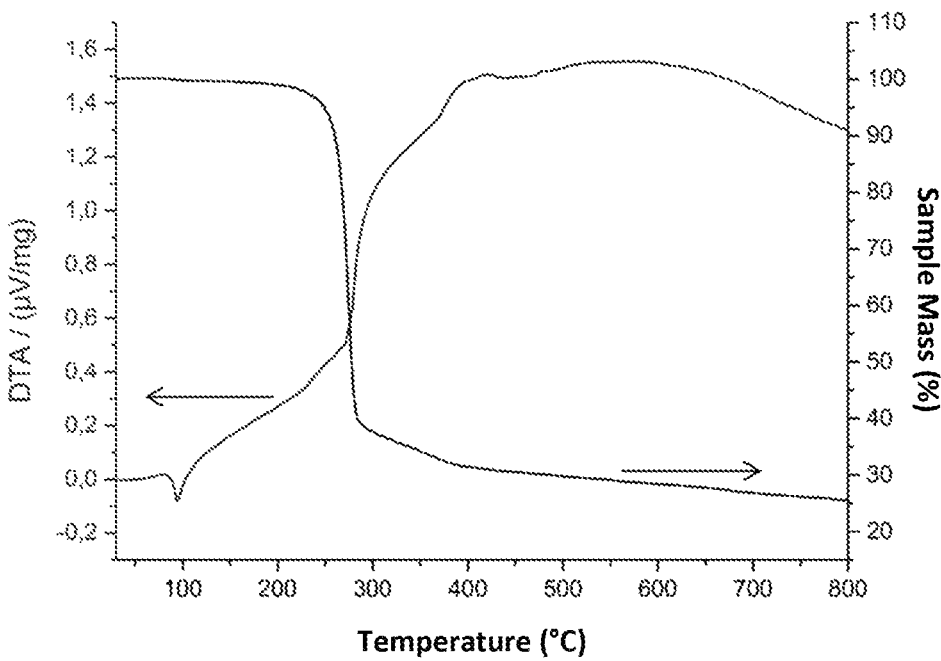
FIG. 4 is a chart showing a differential thermal analysis (DTA) and a thermogravimetry analysis for Compound C4 of Example 4.

The differential thermal analysis and the thermogravimetry analysis of C4 are depicted in FIG. 4. The DTA shows an endothermic peak at 80° C. Deriving from the thermogravimetry analysis, the sample has lost 62.4% of its mass at 380° C. and 75.3% at 800° C.

Example 5

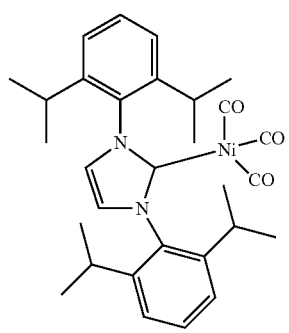

C5

In a dropping funnel were weighed 1.00 g (5.86 mmol, 0.76 mL) [Ni(CO)$_4$] and mixed with 10 mL hexane. This mixture is added dropwise to a suspension of 1.00 g (2.57 mmol) Dipp$_2$Im in 20 mL hexane. After 3 h stirring all volatiles of the yellowish clear solution are removed and the solid is placed on a frit, washed twice with 5 mL hexane and dried in vacuo to afford 950 mg (74%) of C5 as a colourless solid.

$^1$H NMR (200 MHz, 25° C., C$_6$D$_6$): δ=1.04 (d, 12 H, $^3$J$_{HH}$=6.9 Hz, CH$_3$), 1.35 (d, 12 H, $^3$J$_{HH}$=6.8 Hz, CH$_3$), 2.77 (sept, 4 H, $^3$J$_{HH}$=6.9 Hz, CH$_3$), 6.62 (s, 2 H, NCHCHN), 7.13 (s, 1 H, aryl-H), 7.24-7.31 (m, 2 H, aryl-H).

$^{13}$C NMR (50.3 MHz, 25° C., C$_6$D$_6$): δ=22.8 (s, $^i$Pr—CH$_3$), 25.5 (s, $^i$Pr—CH$_3$), 28.8 (s, $^i$Pr—CH), 123.4 (s, NCCN), 124.3 (s, aryl-C), 130.2 (s, aryl-C), 137.8 (s, aryl-C), 146.0 (s, aryl-C), 197.3 (CO), 197.9 (NCN).

Figure 5:
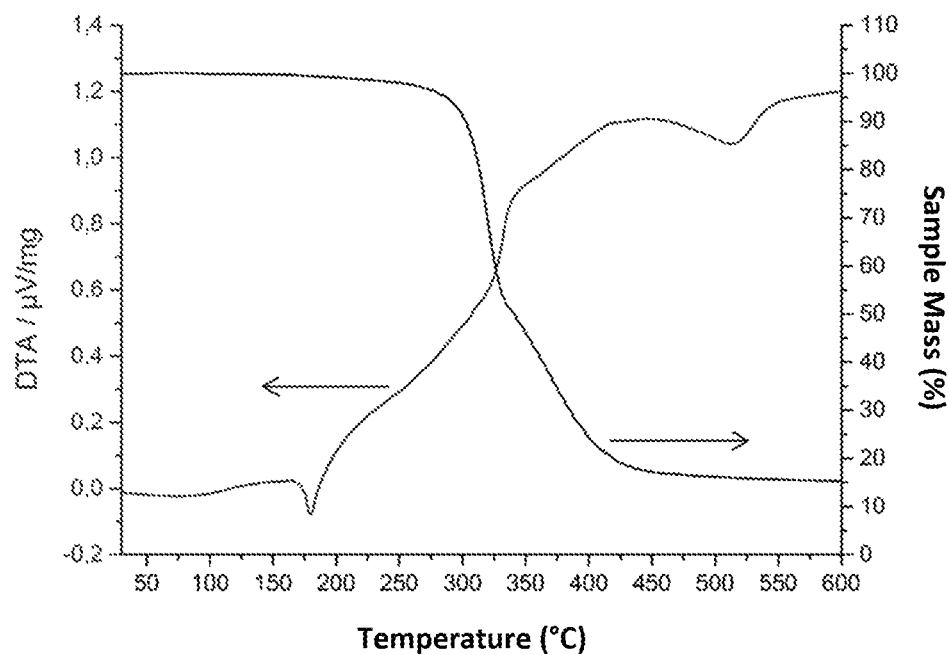
FIG. 5 is a chart showing a differential thermal analysis (DTA) and a thermogravimetry analysis for Compound C5 of Example 5.

The differential thermal analysis and the thermogravimetry analysis of C5 are depicted in FIG. 5. The DTA shows an endothermic peak at 168° C. Deriving from the thermogravimetry analysis, the sample has lost 47.0% of its mass at 330° C. and 86.0% at 600° C.

Example 6

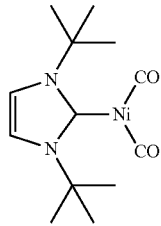

C6

A hexane solution (20 mL) of 2.00 g (11.1 mmol) $^t$Bu$_2$Im was added dropwise to a hexane solution (20 mL) of 3.82 g (22.4 mmol, 2.90 mL) [Ni(CO)$_4$]. After stirring 3 h the volatiles were removed and the resulting red solid was suspended in −78° C. cold pentane, filtered off and dried in vacuo to afford 2.80 g (86%) of C6.

$^1$H NMR (200 MHz, 25° C., C$_6$D$_6$): δ=1.41 (s, 18 H, tBu-CH$_3$), 6.56 (s, 2 H, NCHCHN).

$^{13}$C NMR (50.3 MHz, 25° C., C$_6$D$_6$): δ=29.9 (s, tBu-CH$_3$), 56.8 (s, tBu-C), 116.9 (s, NCCN), 189.4 (CO), 197.8 (NCN).

Figure 6:
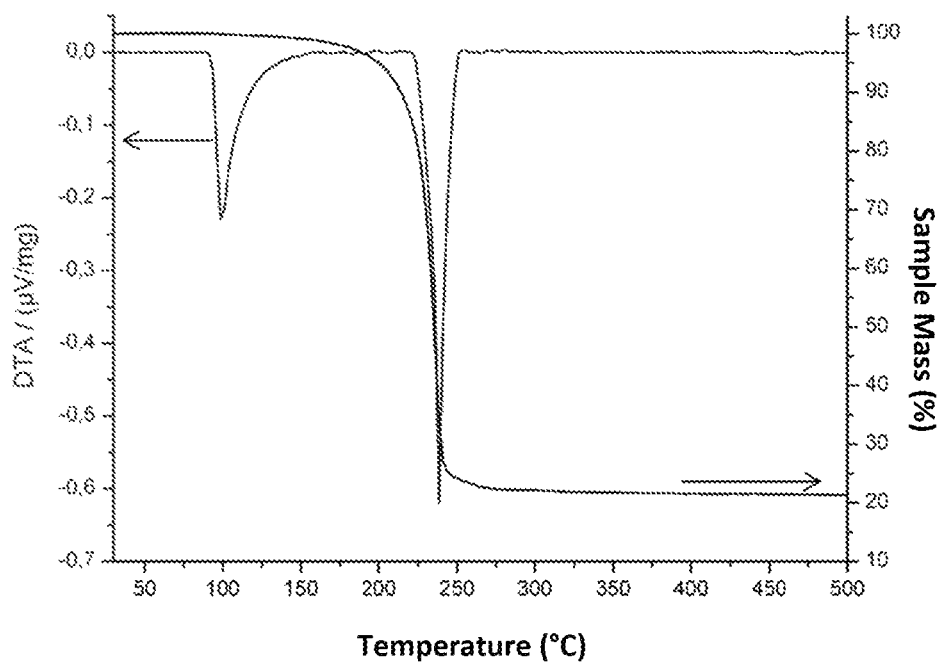
FIG. 6 is a chart showing a differential thermal analysis (DTA) and a thermogravimetry analysis for Compound C6 of Example 6.

The differential thermal analysis and the thermogravimetry analysis of C6 are depicted in FIG. 6. The DTA shows two endothermic peak at 89° C. and 223° C. respectively. Deriving from the thermogravimetry analysis, the sample has lost 79.0% of its mass at 500° C.

Example 7

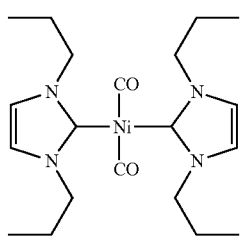

C7

Compound C7 was synthesized and characterized according to T. Schaub et al., Organometallics, volume 25 (2006), pages 4196-4206.

Figure 7:
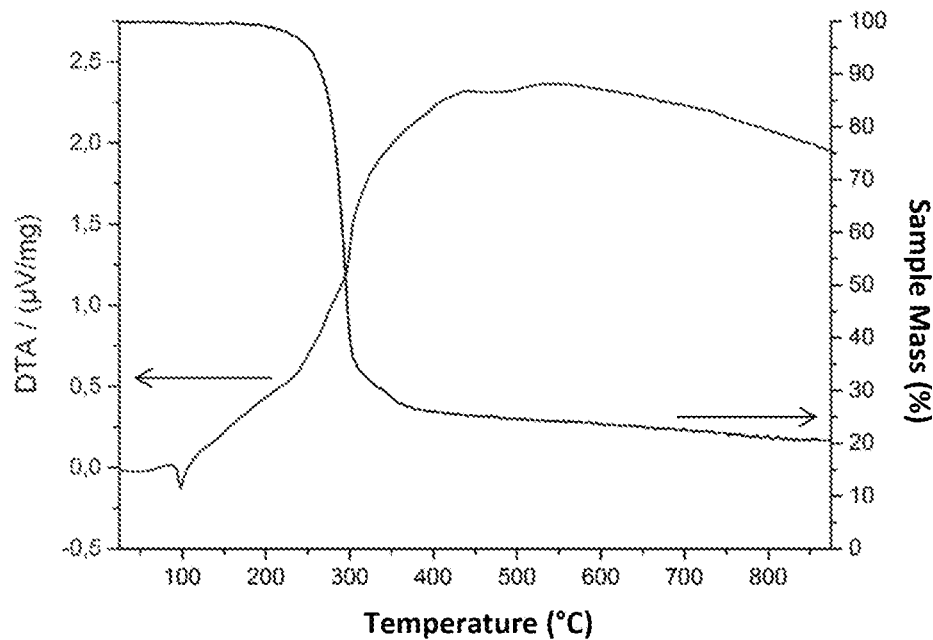
FIG. 7 is a chart showing a differential thermal analysis (DTA) and a thermogravimetry analysis for Compound C7 of Example 7.

The differential thermal analysis and the thermogravimetry analysis of C7 are depicted in FIG. 7. The DTA shows an endothermic peak at 90° C. Deriving from the thermogravimetry analysis, the sample has lost 65.7% of its mass at 300° C. and 73.4% at 420° C.

Example 8

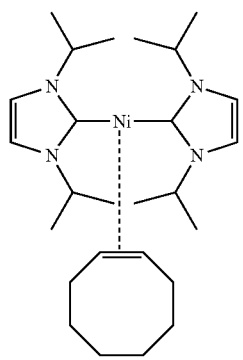

C8

Compound C8 was synthesized and characterized according to P. Fischer et al., Zeitschrift für Allgemeine and Anorganische Chemie, volume 638 (2012), pages 1491-1496.

Figure 8:
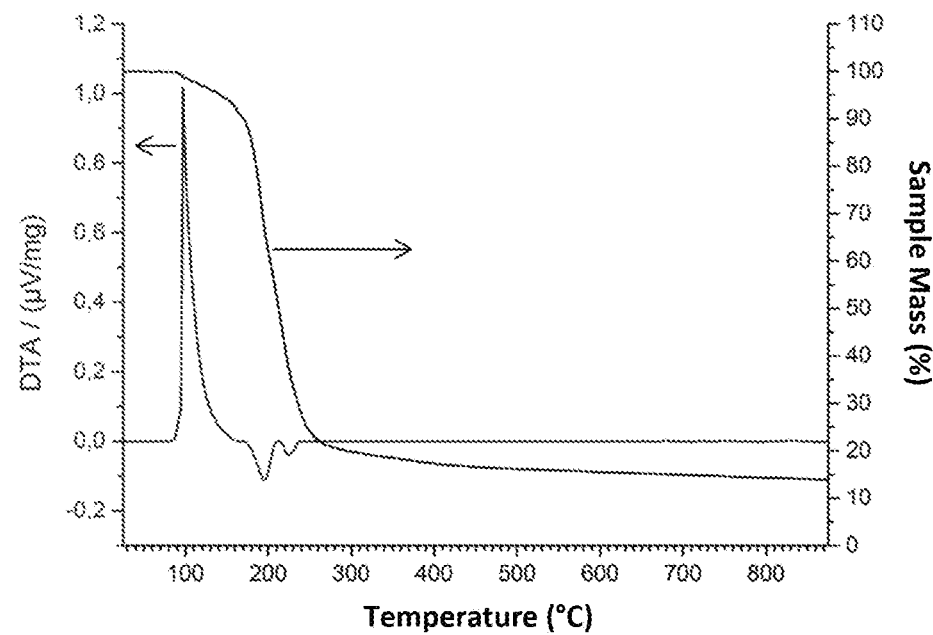
FIG. 8 is a chart showing a differential thermal analysis (DTA) and a thermogravimetry analysis for Compound C8 of Example 8.

The differential thermal analysis and the thermogravimetry analysis of C8 are depicted in FIG. 8. The DTA shows an exothermic peak at 85° C. and two endothermic peaks at 175° C. and 218° C. respectively. Deriving from the thermogravimetry analysis, the sample has lost 86.1% of its mass at 800° C.

Example 9

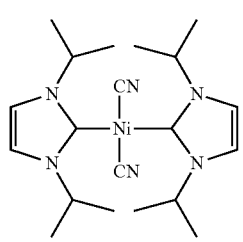

C9

Compound C9 was synthesized and characterized according to P. Fischer et al., Dalton Transactions, (2007), pages 1993-2002.

Figure 9:
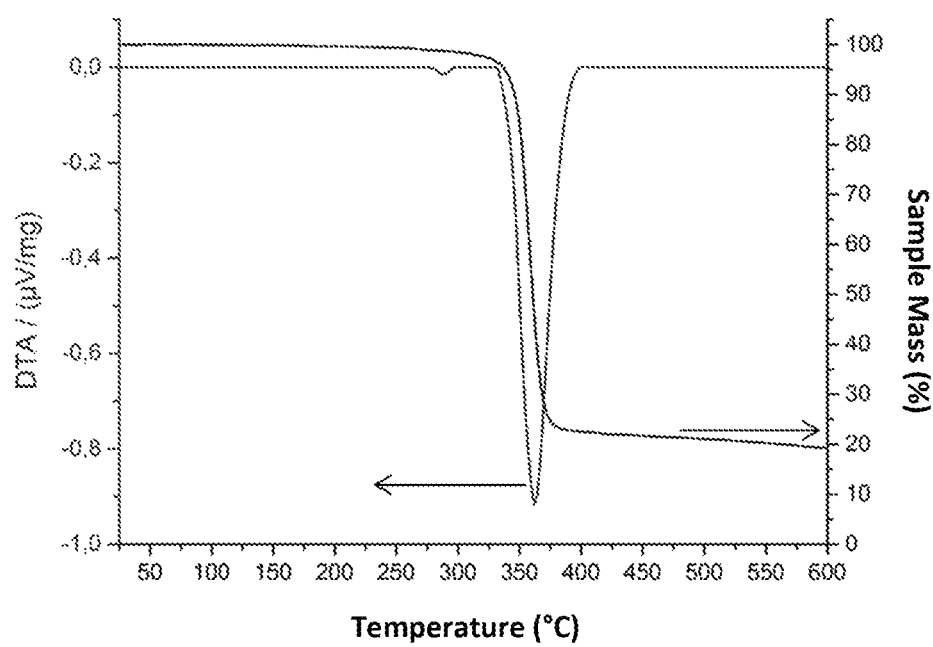
FIG. 9 is a chart showing a differential thermal analysis (DTA) and a thermogravimetry analysis for Compound C9 of Example 9.

The differential thermal analysis and the thermogravimetry analysis of C9 are depicted in FIG. 9. The DTA shows two exothermic peaks at 278° C. and 335° C. respectively. Deriving from the thermogravimetry analysis, the sample has lost 69% of its mass at 600° C.

Example 10

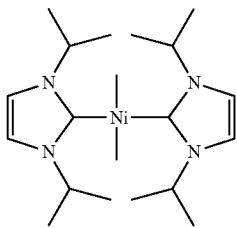

C10

Compound C10 was synthesized and characterized according to P. Fischer et al., Zeitschrift für Allgemeine and Anorganische Chemie, volume 638 (2012), pages 1491-1496.

Figure 10:
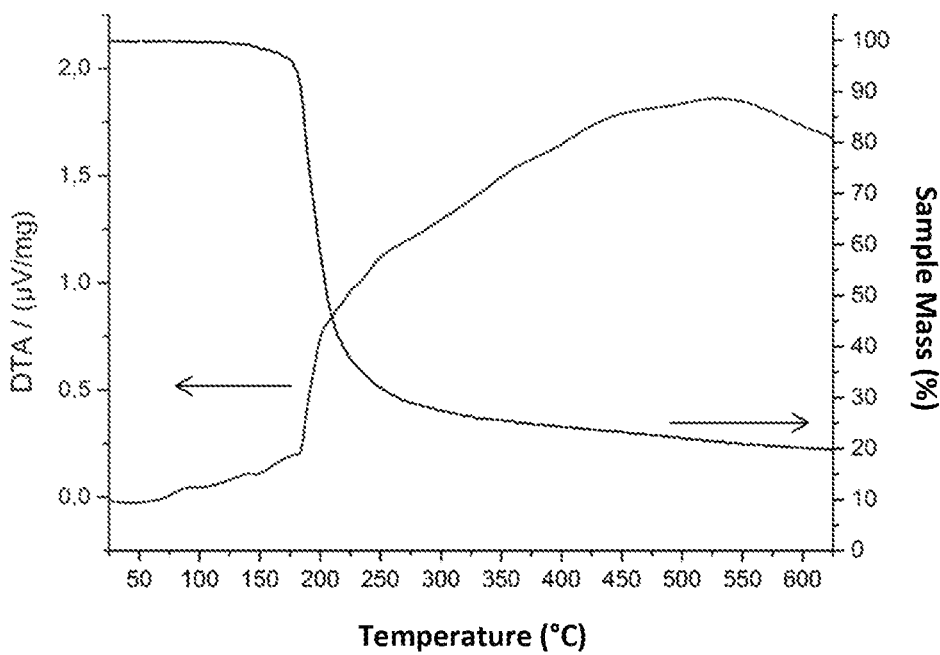
FIG. 10 is a chart showing a differential thermal analysis (DTA) and a thermogravimetry analysis for Compound C10 of Example 10.

The differential thermal analysis and the thermogravimetry analysis of C10 are depicted in FIG. 10. The DTA shows an exothermic peak at 90° C. and an endothermic peak at 182° C. Deriving from the thermogravimetry analysis, the sample has lost 82.3% of its mass at 600° C.

Example 11

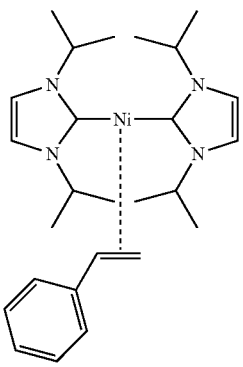

C11

To a suspension of 200 mg (0.72 mmol) [Ni(COD)$_2$] in 10 mL thf were added 82.0 µL (0.72 mmol, 74.6 mg) styrene. After stirring for 5 minutes 218 µL (1.43 µL, 218 mg) $^i$Pr$_2$Im were added and the mixture is stirred for 1 h. All volatile material is removed in vacuo, the residue is solved in hexane (10 mL), cooled to −80° C. for 16 h, filtered off and dried in vacuo. C11 is obtained as an orange powder (250 mg, 75%).

$^1$H NMR (500 MHz. C$_6$D$_6$, 25° C.): δ=0.94 (d, 6 H, $^3J_{HH}$=6.8 Hz, $^i$Pr—CH$_3$), 1.07 (d, 6 H, $^3J_{HH}$=6.8 Hz, $^i$Pr—CH$_3$), 1.11 (d, 6 H, $^3J_{HH}$=6.8 Hz, $^i$Pr—CH$_3$), 1.23 (d, 6 H, $^3J_{HH}$=6.8 Hz, $^i$Pr—CH$_3$), 2.12 (d, 2 H, $^3J_{HH}$=9.9 Hz, CHCH$_2$) 3.75 (t, 1 H, $^3J_{HH}$=9.9 Hz, CHCH$_2$), 5.32 (sept, $^3J_{HH}$=6.8 Hz, $^i$Pr—CH), 5.52 (sept, $^3J_{HH}$=6.8 Hz, $^i$Pr—CH), 6.36 (s, 2 H, NCHCHN), 6.48 (s, 2 H, NCHCHN), 6.88 (m, 1 H, aryl-CH), 7.14-7.28 (m, 4 H, aryl-CH).

$^{13}$C NMR (128 MHz, C$_6$D$_6$, 25° C.): δ=22.8 ($^i$Pr—CH$_3$), 23.1 ($^i$Pr—CH$_3$), 23.4 ($^i$Pr—CH$_3$), 23.7 ($^i$Pr—CH$_3$), 24.6 (CHCH$_2$), 45.7 (CHCH$_2$), 51.0 ($^i$Pr—CH), 51.2 ($^i$Pr—CH), 114.7 (NCCN), 114.8 (NCCN), 118.6 (aryl-CH), 123.6 (aryl-CH), 128.2 (aryl-CH) 153.3 (aryl-C), 200.8 (NCN), 202.9 (NCN).

Figure 11:
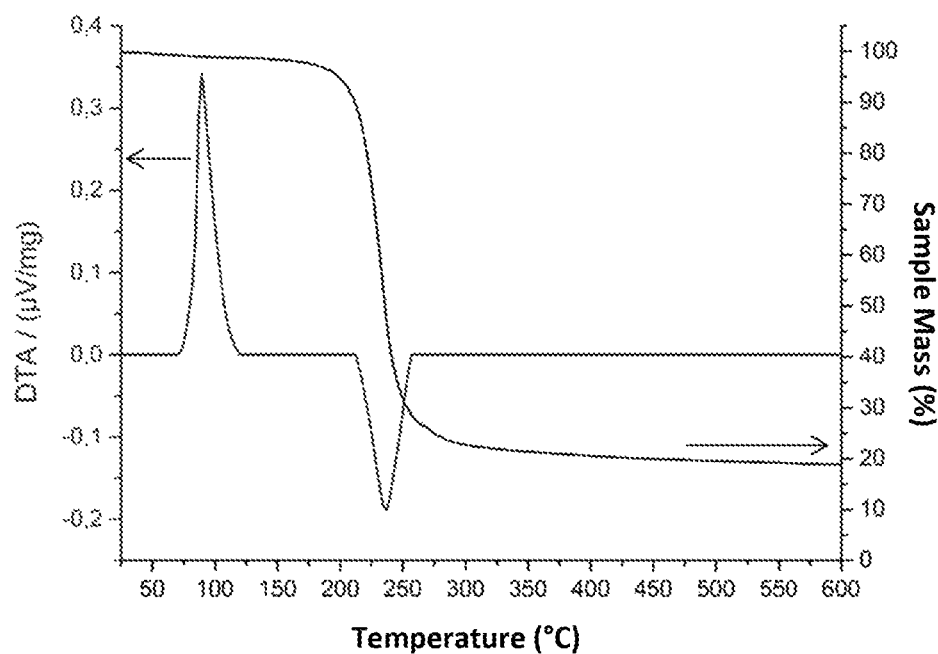
FIG. 11 is a chart showing a differential thermal analysis (DTA) and a thermogravimetry analysis for Compound C11 of Example 11.

The differential thermal analysis and the thermogravimetry analysis of C11 are depicted in FIG. 11. The DTA shows an exothermic peak at 68° C. and an endothermic peak at 214° C. Deriving from the thermogravimetry analysis, the sample has lost 77.8% of its mass at 600° C.

Example 12

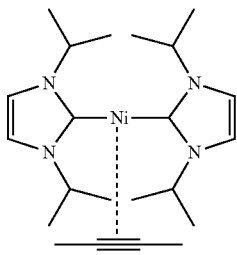

C12

Compound C12 was synthesized and characterized according to T. Schaub et al., Organometallics, volume 25 (2006), pages 4196-4206.

Figure 12:
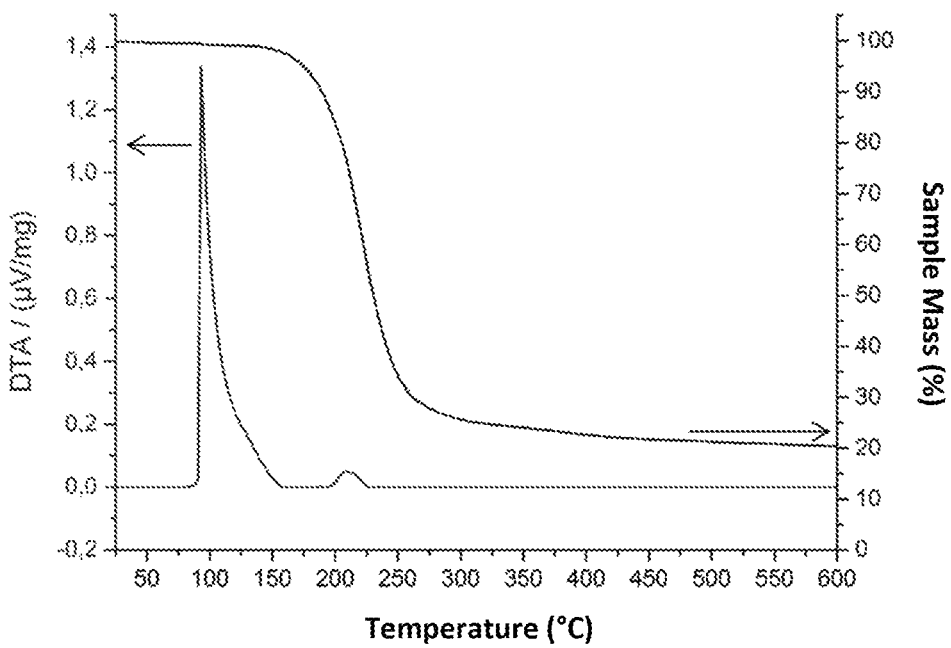
FIG. 12 is a chart showing a differential thermal analysis (DTA) and a thermogravimetry analysis for Compound C12 of Example 12.

The differential thermal analysis and the thermogravimetry analysis of C12 are depicted in FIG. 12. The DTA shows two exothermic peaks at 86° C. and 192° C. respectively. Deriving from the thermogravimetry analysis, the sample has lost 81% of its mass at 600° C.

Example 13

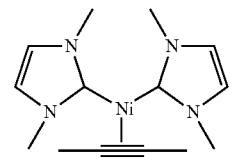

C13

430 mg (3.18 mmol) KC$_8$ were added to a cooled mixture (0° C.) of 500 mg (991 µmol) [Ni(Me$_2$Im)$_2$I$_2$], 116 µL (1.49 mmol, 80.4 mg) 2-butyne and 15 mL thf. After stirring over night and warming to ambient temperature the reaction mixture was filtered over a pad of celite, washed twice (20 mL thf) and the filtrate was dried in vacuo. The residue was solved in 20 mL toluene, filtered and all volatile material of the mother liquor was removed in vacuo. The brown solid was suspended in 20 mL hexane, cooled to −80° C. for 16 h and filtered off to afford 200 mg (66%) of C13.

$^1$H NMR (500 MHz. C$_6$D$_6$, 25° C.): δ=2.70 (s, 6 H, alkyne-CH$_3$), 3.45 (s, 12 H, CH$_3$), 6.24 (s, 4 H, NCHCHN).

$^{13}$C NMR (128 MHz, C$_6$D$_6$, 25° C.): δ=13.9 (alkyne-CH$_3$), 36.7 (CH$_3$), 119.1 (NCCN), 121.8 (alkyne-CC), 207.0 (NCN).

Figure 13:
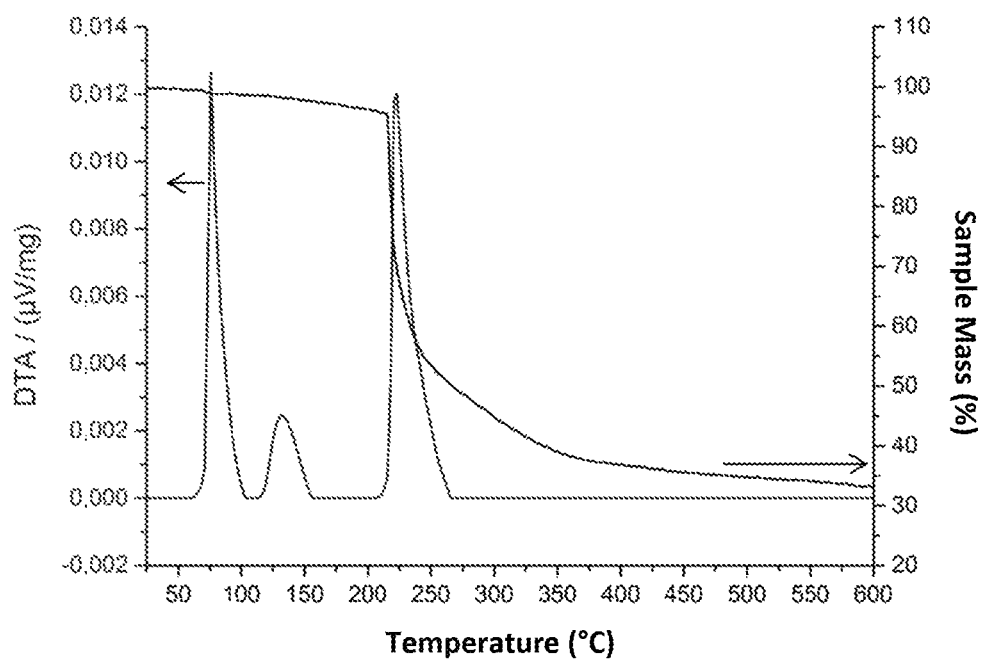
FIG. 13 is a chart showing a differential thermal analysis (DTA) and a thermogravimetry analysis for Compound C13 of Example 13.

The differential thermal analysis and the thermogravimetry analysis of C13 are depicted in FIG. 13. The DTA shows three exothermic peaks at 69° C., 118° C. and 225° C. respectively. Deriving from the thermogravimetry analysis, the sample has lost 81% of its mass at 600° C.

Example 14

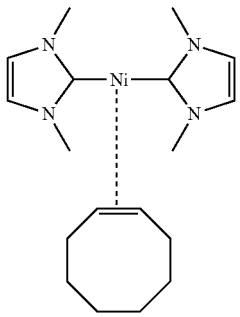

C14

500 mg (1.00 mmol) [Ni(Me$_2$Im)$_2$I$_2$] were suspended in 20 mL thf (0° C.), mixed with 0.16 mL (1.20 mmol, 134 mg) and 430 mg (3.18 mmol) KC$_8$. The reaction mixture was stirred for 16 h at ambient temperature, filtered over a pad of celite, washed four times with thf (5 mL) and the filtrate was dried in vacuo. The residue is solved in 20 mL toluene, filtered and all volatile material is removed. The yellow solid was suspended in hexane (10 mL), cooled to 0° C., filtered and dried in vacuo to give 170 mg (47%) of [Ni(Me$_2$Im)$_2$($\eta^2$-COE)] of C14.

$^1$H NMR (500 MHz. C$_6$D$_6$, 25° C.): δ=1.73 (m, 4 H, COE-CH$_2$), 1.90 (m, 2 H, COE-CH$_2$), 2.10 (m, 4 H, COE-CH$_2$), 2.29 (m, 2 H, COE-CH$_2$), 2.54 (m, 2 H, COE-CH), 3.43 (s, 12 H, CH$_3$), 6.24 (s, 4 H, NCHCHN).

$^{13}$C NMR (128 MHz, C$_6$D$_6$, 25° C.): η=27.7 (COE-CH$_2$), 30.6 (COE-CH$_2$), 33.5 (COE-CH$_2$), 36.8 (CH$_3$), 48.3 (COE-CH), 128.1 (NCCN), 208.6 (NCN).

Figure 14:
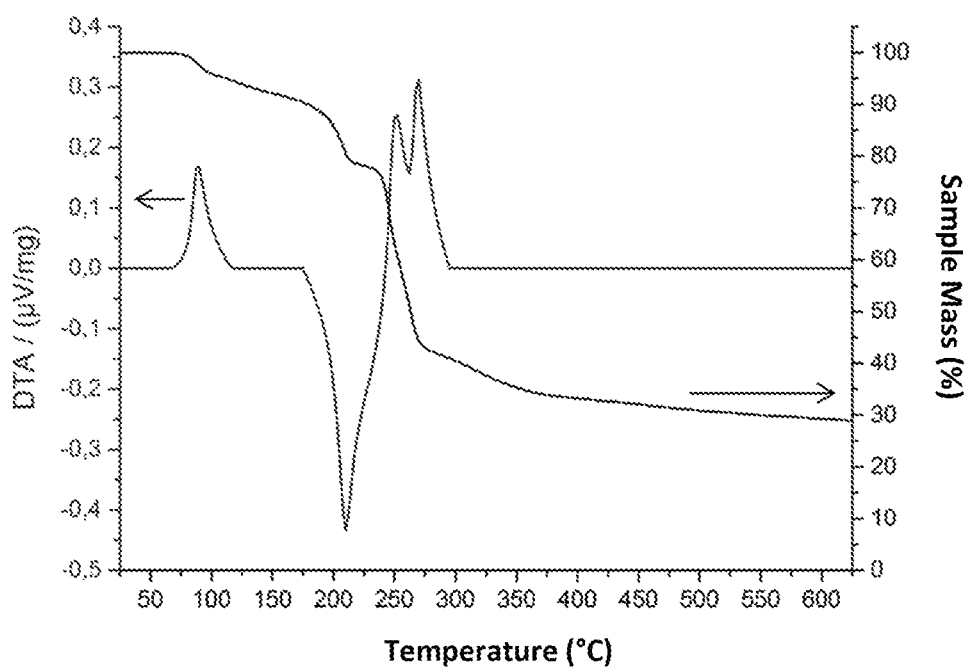
FIG. 14 is a chart showing a differential thermal analysis (DTA) and a thermogravimetry analysis for Compound C14 of Example 14.

The differential thermal analysis and the thermogravimetry analysis of C14 are depicted in FIG. 14. The DTA shows an exothermic peak at 71° C. and three endothermic peaks at 185° C., 234° C. and 263° C. respectively. Deriving from the thermogravimetry analysis, the sample has lost 5% of its mass at 100° C., 21% at 200° C., 46.7% at 260° C., 55.7° C. at 350° C. and 69.9% at 600° C.

Example 15

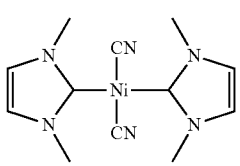

C15

To a suspension of 333 mg (0.66 mmol) [Ni(Me$_2$Im)$_2$I$_2$] in 20 mL thf were added 0.21 mL (1.65 mmol, 164 mg) trimethylsilyl cyanide in one portion. After 2 days stirring the residue was filtered of, washed twice with thf (10 mL) and dried in vacuo to afford C15 (198 mg, 99%) as an off-white powder.

$^1$H NMR (200 MHz. CD$_2$Cl$_2$, 25° C.): δ=4.10 (s, 12 H, CH$_3$), 6.95 (s, 4 H, NCHCHN).

$^{13}$C NMR (128 MHz, CD$_2$Cl$_2$, 25° C.): δ=38.0 (CH$_3$), 123.2 (NCCN), 131.9 (Ni—CN), 173.6 (NCN).

Figure 15:
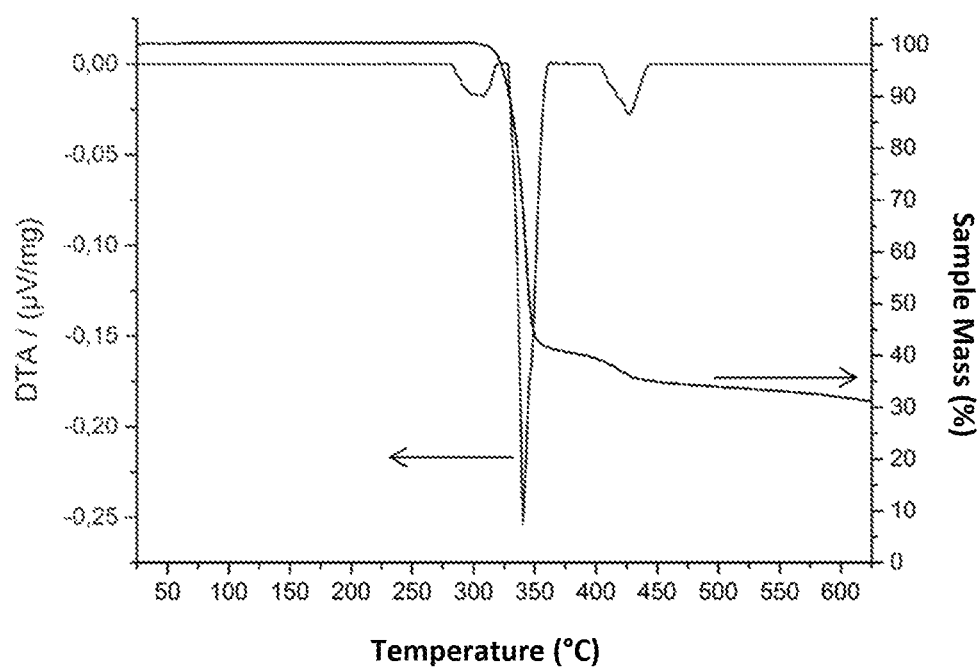
FIG. 15 is a chart showing a differential thermal analysis (DTA) and a thermogravimetry analysis for Compound C15 of Example 15.

The differential thermal analysis and the thermogravimetry analysis of C15 are depicted in FIG. 15. The DTA shows three endothermic peaks at 275° C., 328° C. and 405° C. respectively. Deriving from the thermogravimetry analysis, the sample has lost 65.9% of its mass at 340° C. and 84.3% at 600° C.

Example 16

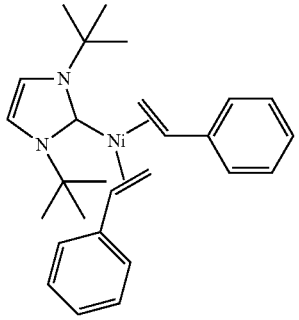

C16

To a suspension of 2.00 g (7.27 mmol) [Ni(COD)$_2$] in 50 mL thf were added dropwise 6.66 ml (58.2 mmol, 6.06 g) styrene. The mixture was stirred at ambient temperature for 25 minutes and a solution of 1.31 g (7.27 mmol) $^t$Bu$_2$Im in 20 mL thf was added dropwise. After stirring for 16 h the mixture was filtered over a pad of celite and the filtrate was dried in vacuo. The orange residue was solved in 50 mL hexane, stored at −80° C. for 16 h and filtered off to afford 2.05 g (63%) of C16.

exo, exo-isomer:
$^1$H NMR (200 MHz, C$_6$D$_6$, 25° C.): δ=1.15 (s, 18 H, $^t$Bu-CH$_3$), 2.92 (dd, 2 H, $^2J_{HH}$=3.1 Hz, trans-$^3J_{HH}$=13.3 Hz, CH$_2$), 3.01 (dd, 2 H, $^2J_{HH}$=3.1 Hz, cis-$^3J_{HH}$=9.4 Hz, CH$_2$), 4.27 (dd, 2 H, cis-$^3J_{HH}$=9.4 Hz, trans-$^3J_{HH}$=13.3 Hz, CHCH$_2$), 6.67 (s, 2 H, NCHCHN), 6.90-7.24 (m, 10 H, aryl-CH).

$^{13}$C NMR (50.3 MHz, C$_6$D$_6$, 25° C.): δ=31.4 (tBu-CH$_3$), 48.9 (CH$_2$), 57.1 (tBu-CCH$_3$), 67.0 (CHCH$_2$), 119.0 (NCCN), 123.3 (aryl-CH), 125.7 (aryl-CH), 125.8 (aryl-CH), 128.4 (aryl-CH), 147.1 (aryl-C), 195.8 (NCN).

exo, endo-isomer:
$^1$H NMR (200 MHz, C$_6$D$_6$, 25° C.): δ=0.91 (s, 9 H, tBu-CH$_3$), 1.37 (s, 9 H, tBu-CH$_3$), 2.41 (dd, 2 H, $^2J_{HH}$=3.2 Hz, cis-$^3J_{HH}$=9.5 Hz, CH$_2$), 3.24 (dd, 2 H, $^2J_{HH}$=3.2 Hz, trans-$^3J_{HH}$=13.4 Hz, CH$_2$), 4.40 (dd, 2 H, cis-$^3J_{HH}$=9.5 Hz, trans-$^3J_{HH}$=13.4 Hz, CHCH$_2$), 6.61 (d, 1 H, $^3J_{HH}$=2.1 Hz, NCHCHN), 6.72 (d, 1 H, $^3J_{HH}$=2.1 Hz, NCHCHN), 6.90-7.24 (m, 10 H, aryl-CH).

$^{13}$C NMR (50.3 MHz, C$_6$D$_6$, 25° C.): δ=31.1 (tBu-CH$_3$), 31.8 (tBu-CH$_3$), 50.2 (CH$_2$), 57.1 (tBu-C(CH$_3$)$_3$), 67.0 (CHCH$_2$), 118.8 (NCCN), 119.5 (NCCN), 123.3 (aryl-CH), 125.7 (aryl-CH), 125.8 (aryl-CH), 128.4 (aryl-CH), 147.1 (aryl-C), 195.5 (NCN).

Figure 16:
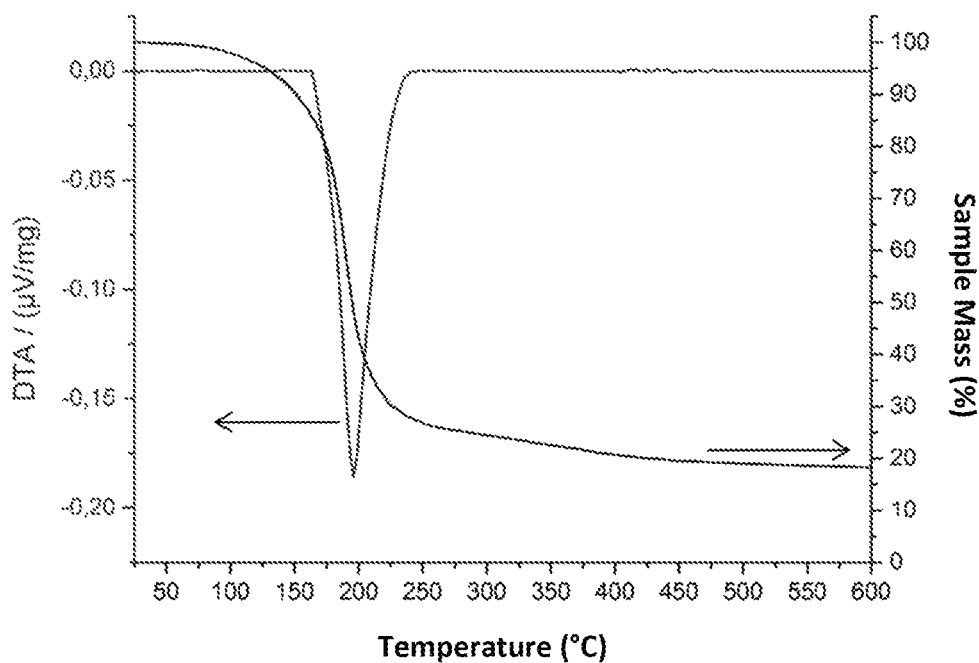
FIG. 16 is a chart showing a differential thermal analysis (DTA) and a thermogravimetry analysis for Compound C16 of Example 16.

The differential thermal analysis and the thermogravimetry analysis of C16 are depicted in FIG. 16. The DTA shows an endothermic peak at 175° C. Deriving from the thermogravimetry analysis, the sample has lost 84.3% of its mass at 600° C.

Example 17

General Procedure for Examples 17 to 22

2.2 eq of the corresponding ligand L$^1$ was dissolved in diethyl ether and 1.0 eq of a stock solution of [Co(CO)$_3$ (NO)] in diethyl ether (50-80 mg/mL) was added. Extrusion of CO starts immediately after addition of the metal complex. The solution was stirred at room temperature overnight and a red precipitate formed in most cases. The volatile components were removed in vacuo and the residue was suspended in a minimum amount of n-pentane. After filtration the product was washed two times with a minimum amount of n-pentane and dried.

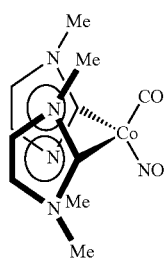

[Co(IMe)$_2$(CO)(NO)]

scale: [Co(CO)$_3$(NO)] 4.48 g (25.9 mmol, added neat); Me$_2$Im 5.48 g (57.0 mmol).

yield: 6.49 g (21.0 mmol, 81%) of a ruby coloured solid.

$^1$H-NMR (500 MHz, C$_6$D$_6$): δ=3.16 (s, 12 H, CH$_3$), 6.12 (s, 4 H, CHCH).

$^{13}$C{$^1$H}-NMR (126 MHz, C$_6$D$_6$): δ=38.0 (CH$_3$), 121.3 (CHCH), 201.9 (br, NCN).

The metal-bound carbonyl carbon was not detected.

CHN for [Co(IMe)$_2$(CO)(NO)] [C$_{11}$H$_{15}$CoN$_5$O$_2$] [309.22 g/mol] calcd. (found): C, 42.73 (42.88); H, 5.22 (5.15); N, 22.65 (22.90).

IR: (ATR): û [cm$^{-1}$]=712 (m), 723 (m), 747 (w), 1001 (w), 1075 (m), 1109 (m), 1223 (s), 1299 (w), 1339 (m), 1364 (s), 1397 (s), 1420 (m), 1445 (s), 1457 (m), 1472 (m), 1489 (w), 1497 (w), 1613 (vs, ν$_{—N=O, str.}$), 1873 (vs, ν$_{—C=O, str.}$), 2949 (vw, ν$_{—C—H, str.}$).

Sublimation: 100° C. at 10$^{-2}$ mbar.

Figure 17:
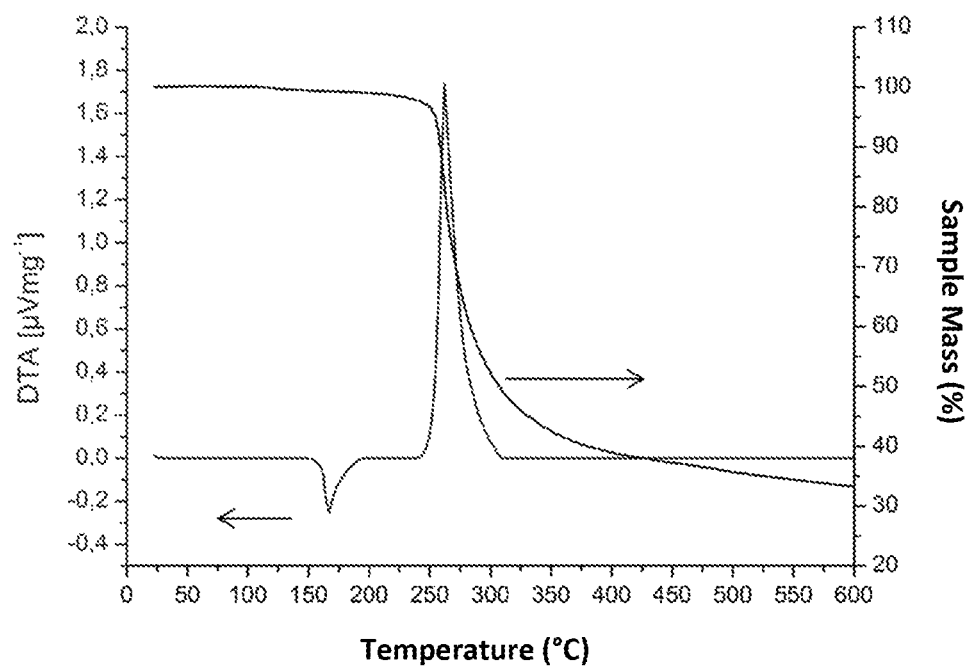
FIG. 17 is a chart showing a differential thermal analysis (DTA) and a thermogravimetry analysis for Compound C17 of Example 17.

The differential thermal analysis (DTA) and the thermogravimetry analysis of C17 are depicted in FIG. 17. The DTA shows an exothermic peak at 262° C. and an endothermic peak at 167° C. Deriving from the thermogravimetry analysis, the sample has lost 66.8% of its mass at 600° C.

Example 18

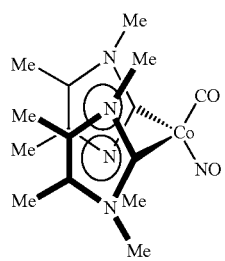

scale: [Co(CO)$_3$(NO)] 150 mg (870 μmol, 50 mg/mL in Et$_2$O); Me$_2$(Me$_2$)Im 237 mg (1.91 mmol).

yield: 220 mg (602 μmol, 69%) of a ruby coloured solid.

$^1$H-NMR (500 MHz, C$_6$D$_6$): δ=1.46 (s, 12 H, CCH$_3$), 3.32 (s, 12 H, NCH$_3$).

$^{13}$C{$^1$H}-NMR (126 MHz, C$_6$D$_6$): δ=9.1 (CCH$_3$), 35.0 (NCH$_3$), 124.5 (CMe), 199.0 (br, NCN). The metal-bound carbonyl carbon was not detected.

CHN for [Co($^{Me}$IMe)$_2$(CO)(NO)] [C$_{15}$H$_{24}$CoN$_5$O$_2$] [365.38 g/mol] calcd. (found): C, 49.32 (49.00); H, 6.49 (6.47); N, 19.17 (19.17).

IR: (ATR): u [cm$^{-1}$]=849 (vw), 1074 (w), 1357 (m), 1387 (w), 1400 (w), 1424 (m), 1457 (w), 1620 (vs, ν$_{—N=O, str.}$), 1865 (vs, ν$_{—C=O, str.}$), 2949 (vw, ν$_{—C—H, str.}$).

Sublimation: 120° C. at 10$^{-2}$ mbar.

Figure 18:
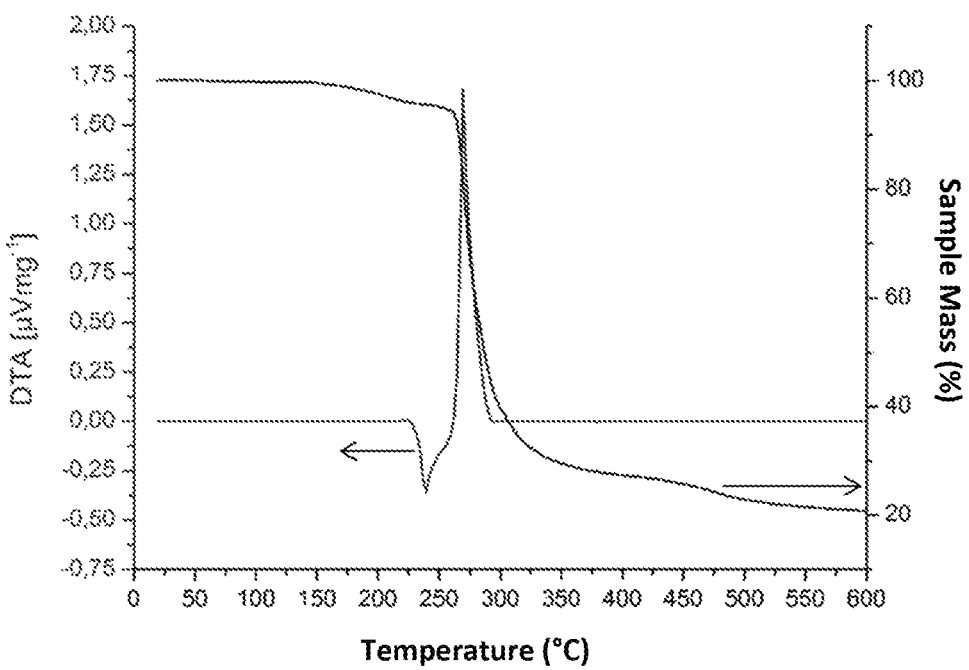
FIG. 18 is a chart showing a differential thermal analysis (DTA) and a thermogravimetry analysis for Compound C18 of Example 18.

The differential thermal analysis (DTA) and the thermogravimetry analysis of C18 are depicted in FIG. 18. The DTA shows an exothermic peak at 270° C. and an endothermic peak at 240° C. Deriving from the thermogravimetry analysis, the sample has lost 79.3% of its mass at 600° C.

Example 19

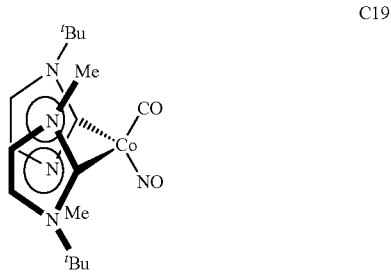

scale: [Co(CO)$_3$(NO)] 200 mg (1.16 mmol, 50 mg/mL in Et$_2$O); Me-t-BuIm 324 mg (2.31 mmol).

yield: 265 mg (674 μmol, 58%) of a purple coloured solid.

$^1$H-NMR (500 MHz, C$_6$D$_6$): δ=1.76 (s, 18 H, C(CH$_3$)$_3$), 2.89 (sbr, 6 H, NCH$_3$), 6.15 (br, 2 H, MeNCH), 6.70 (d, 2 H, tBuNCH, $^3$J$_{HH}$=2.0 Hz).

$^{13}$C{$^1$H}-NMR (126 MHz, C$_6$D$_6$): δ=30.5 (C(CH$_3$)$_3$), 38.6 (NCH$_3$), 58.6 (CMe$_3$), 118.6 (tBuNCH), 120.6 (br, MeNCH) 199.5 (br, NCN), 221.4 (br, CO).

The metal-bound carbonyl carbon was not detected.

CHN for [Co(IMe$^t$Bu)$_2$(CO)(NO)] [C17H$_{28}$CoN$_5$O$_2$] [393.38 g/mol] calcd. (found): C, 51.91 (51.78); H, 7.17 (7.11); N, 17.80 (17.54).

Sublimation: 120° C. at 10$^{-2}$ mbar.

Figure 19:
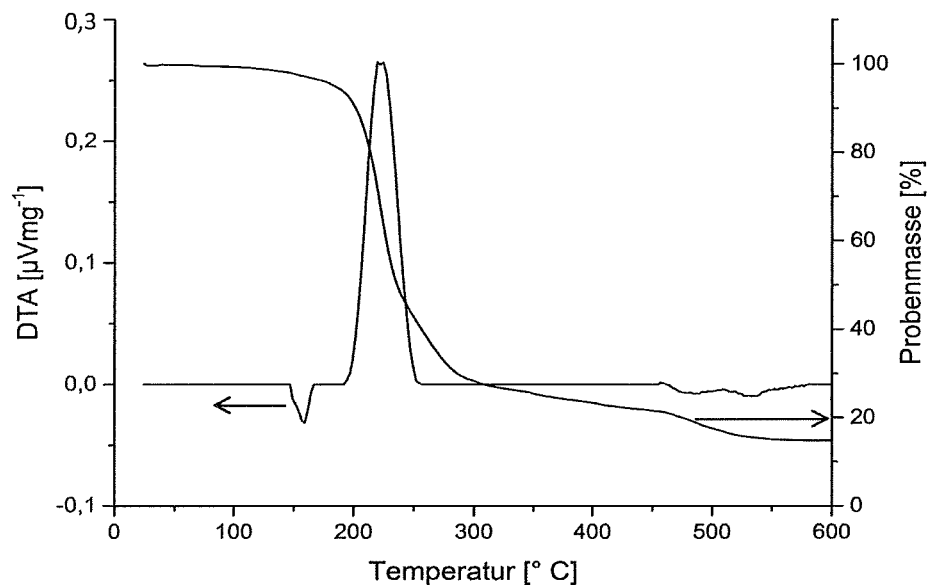
FIG. 19 is a chart showing a differential thermal analysis (DTA) and a thermogravimetry analysis for Compound C19 of Example 19.

The differential thermal analysis (DTA) and the thermogravimetry analysis of C19 are depicted in FIG. 19. The DTA shows an exothermic peak at 222° C. and two endothermic peaks at 159° C. and approx. 500° C. respectively. Deriving from the thermogravimetry analysis, the sample has lost 85.1% of its mass at 600° C.

Example 20

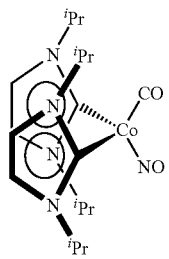

C20 scale: [Co(CO)$_3$(NO)] 6.16 g (35.6 mmol, added neat); i-Pr$_2$Im 11.9 g (78.3 mmol).

yield: 12.8 g (30.4 mmol, 86%) of a ruby coloured solid.

$^1$H-NMR (500 MHz, C$_6$D$_6$): δ=1.00 (d, 12 H, CH$_3$, $^3J_{HH}$=6.8 Hz), 1.06 (d, 12 H, CH$_3$, $^3J_{HH}$=6.8 Hz), 5.23 (sept, 4 H, CHMe$_2$, $^3J_{HH}$=6.8 Hz), 6.52 (s, 4 H, CHCH).

$^{13}$C{$^1$H}-NMR (126 MHz, C$_6$D$_6$): δ=23.0 (CH$_3$), 23.1 (CH$_3$), 51.5 (CHMe$_2$), 116.8 (CHCH), 199.5 (br, NCN).

The metal-bound carbonyl carbon was not detected.

CHN for [Co(I$^i$Pr)$_2$(CO)(NO)] [C$_{19}$H$_{32}$CoN$_5$O$_2$] [421.43 g/mol] calcd. (found): C, 54.15 (54.04); H, 7.65 (7.58); N, 16.62 (16.96).

IR: (ATR): û [cm$^{-1}$]=716 (w), 730 (vw), 883 (vw), 989 (w), 1018 (vw), 1081 (vw), 1135 (w), 1214 (s), 1252 (w), 1286 (w), 1366 (m), 1399 (w), 1415 (w), 1437 (vw), 1457 (w), 1613 (vs, ν$_{N=O, str.}$), 1865 (vs, ν$_{C=O, str.}$), 2982 (w, ν$_{C—H, str.}$).

Sublimation: 100° C. at 10$^{-2}$ mbar.

Figure 20:
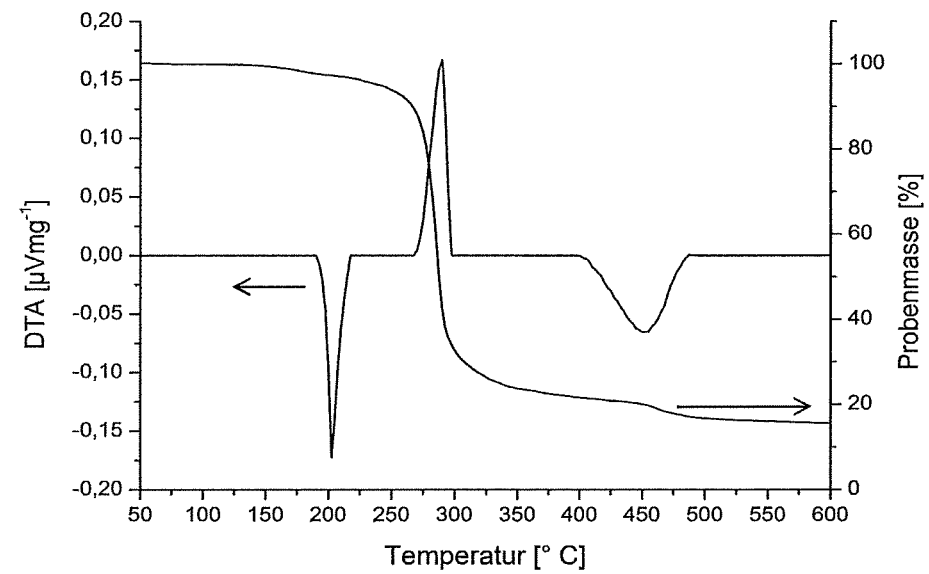
FIG. 20 is a chart showing a differential thermal analysis (DTA) and a thermogravimetry analysis for Compound C20 of Example 20.

The differential thermal analysis (DTA) and the thermogravimetry analysis of C20 are depicted in FIG. 20. The DTA shows an exothermic peak at 290° C. and two endothermic peaks at 203° C. and 450° C. respectively. Deriving from the thermogravimetry analysis, the sample has lost 84.4% of its mass at 600° C.

Example 21

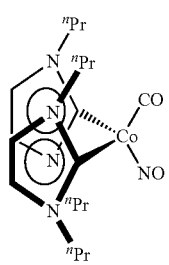

C21 scale: [Co(CO)$_3$(NO)] 200 mg (1.16 µmol, 50 mg/mL in Et$_2$O); n-Pr$_2$Im 457 mg (3.01 mmol).

yield: 388 mg (921 µmol, 80%) of a ruby coloured solid.

$^1$H-NMR (500 MHz, C$_6$D$_6$): δ=0.74 (t, 12 H, CH$_3$, $^3J_{HH}$=7.4 Hz), 1.52 (m, 8 H, MeCH$_2$), 3.79 (m, 8 H, NCH$_2$), 6.36 (s, 4 H, CHCH).

$^{13}$C{$^1$H}-NMR (126 MHz, C$_6$D$_6$): δ=11.3 (CH$_3$), 24.4 (MeCH$_2$), 52.6 (NCH$_2$), 120.5 (CHCH), 200.9 (br, NCN), 222.0 (br, CO).

CHN for [Co(I$^n$Pr)$_2$(CO)(NO)] [C$_{19}$H$_{32}$CoN$_5$O$_2$] [421.43 g/mol] calcd. (found): C, 54.15 (54.57); H, 7.65 (7.58); N, 16.62 (16.74).

Sublimation: 100° C. at 10$^{-2}$ mbar.

Figure 21:
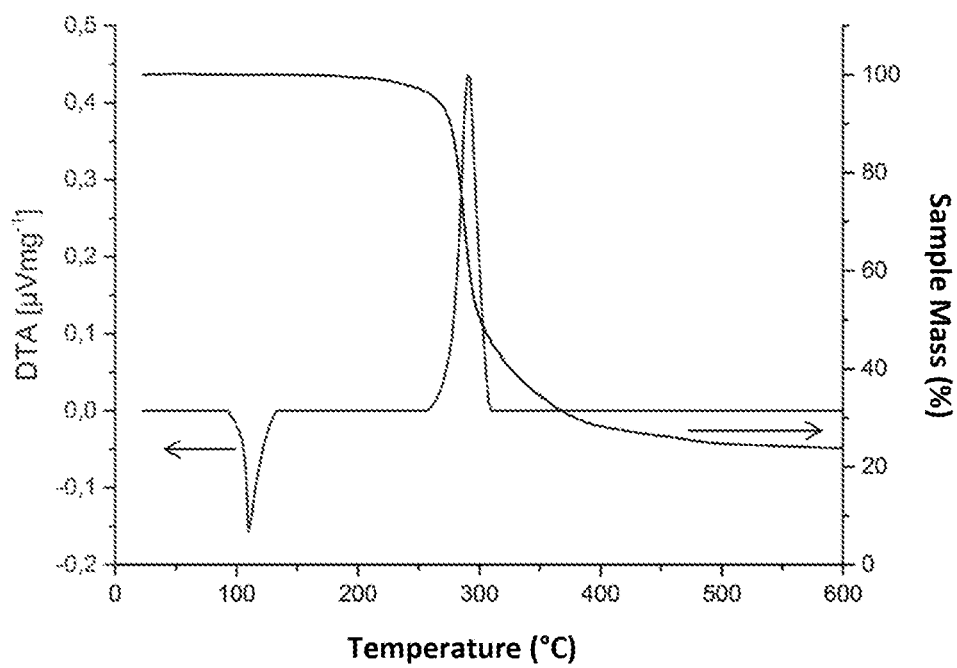
FIG. 21 is a chart showing a differential thermal analysis (DTA) and a thermogravimetry analysis for Compound C21 of Example 21.

The differential thermal analysis (DTA) and the thermogravimetry analysis of C21 are depicted in FIG. 21. The DTA shows two exothermic peak at 290° C. and an endothermic peak at 110° C. Deriving from the thermogravimetry analysis, the sample has lost 76.2% of its mass at 600° C.

Example 22

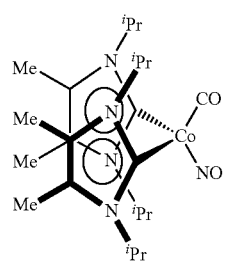

C22 scale: [Co(CO)$_3$(NO)] 200 mg (1.16 mmol, 50 mg/mL in Et$_2$O); iPr$_2$(Me$_2$)Im 419 mg (2.32 mmol).

yield: 430 mg (900 µmol, 78%) of a ruby coloured solid.

$^1$H-NMR (500 MHz, C$_6$D$_6$): δ=1.13 (d, 12 H, CH(CH$_3$)$_2$, $^3J_{HH}$=7.2 Hz), 1.20 (d, 12 H, CH(CH$_3$)$_2$, $^3J_{HH}$=7.2 Hz), 1.80 (s, 12 H, CCH$_3$), 5.85 (sept, 4 H, CHMe$_2$, $^3J_{HH}$=7.2 Hz).

$^{13}$C{$^1$H}-NMR (126 MHz, C$_6$D$_6$): δ=10.5 (CCH$_3$), 21.5 (CH(CH$_3$)$_2$), 53.2 (CH(CH$_3$)$_2$), 125.4 (C(CH$_3$)), 120.3 (MeNCH), 200.3 (br, NCN), 221.1 (br, CO).

CHN for [Co($^{Me}$I$^i$Pr)$_2$(CO)(NO)] [C$_{23}$H$_{40}$CoN$_5$O$_2$] [477.54 g/mol] calcd. (found): C, 57.85 (56.31); H, 8.44 (8.02); N, 14.67 (14.26).

Sublimation: 130° C. at 10$^{-2}$ mbar.

Figure 22:
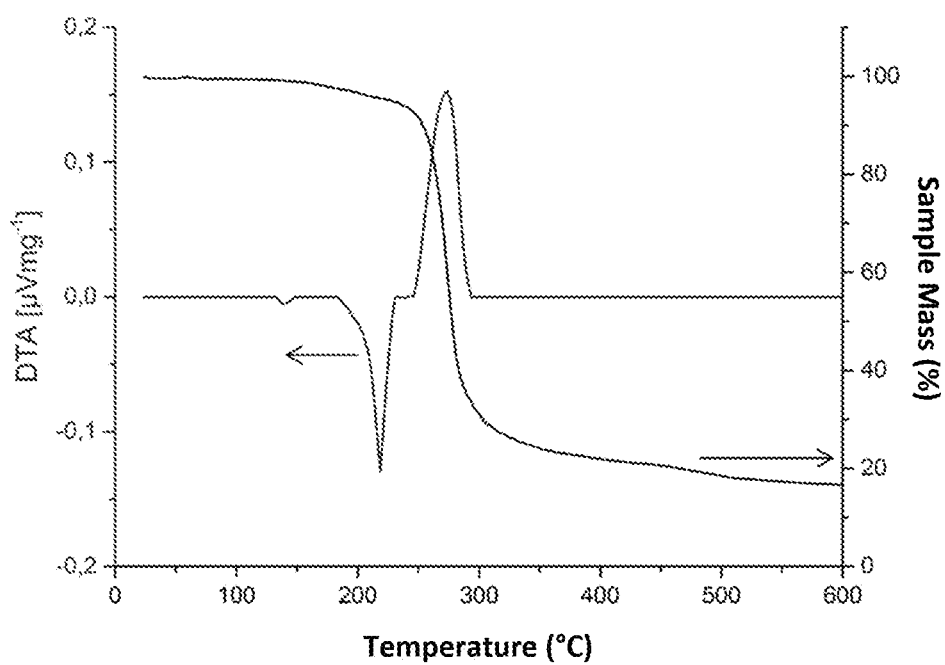
FIG. 22 is a chart showing a differential thermal analysis (DTA) and a thermogravimetry analysis for Compound C22 of Example 22.

The differential thermal analysis (DTA) and the thermogravimetry analysis of C22 are depicted in FIG. 22. The DTA shows an exothermic peak at 274° C. and two endothermic peaks at 139° C. and 219° C. respectively. Deriving from the thermogravimetry analysis, the sample has lost 83.4% of its mass at 600° C.

Example 23

General Procedure for Examples 23 to 31

1.0 eq of a stock solution of [Co(CO)$_3$(NO)] in diethyl ether (50-80 mg/mL) was diluted by diethyl ether and 0.8 eq of the corresponding L$^1$ ligand were added. Extrusion of CO starts immediately after addition of the metal complex. The solution is stirred at room temperature overnight yielding a ruby or orange colored solution.

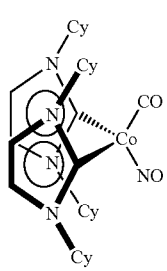

C23 scale: [Co(CO)₃(NO)] 84 mg (490 μmol, 42 mg/mL in Et₂O); Cy₂Im 230 mg (980 μmol).

yield: 197 mg (339 μmol, 69%) of a ruby coloured solid.

¹H-NMR (500 MHz, C₆D₆): δ=0.94, 1.14, 1,22, 1.49, 1.62, 2.05 (40 H, CH₂), 4.84 (t, 2 H, NCH(CH₂)₂, ³J$_{HH}$ (ax,ax)=7.4 Hz, ³J$_{HH}$ (ax,eq)=3.7 Hz), 6.66 (s, 2 H, CHCH).

¹³C{¹H}-NMR (126 MHz, C₆D₆): δ=25.8 (NCHCH₂CH₂), 26.0 (NCHCH₂CH₂), 26.1 (NCHCH₂CH₂CH₂), 34.2 (NCHCH₂), 34.4 (NCHCH₂), 59.2 (NCH), 117.2 (CHCH), 200.4 (br, NCN), 221.6 (br, CO).

CHN for [Co(ICy)₂(CO)(NO)] [C₃₁H₄₈CoN₅O₂] [581.68 g/mol] calcd. (found): C, 54.15 (54.57); H, C, 64.01 (63.43); H, 8.32 (8.18); N, 12.04 (11.82).

Sublimation: 160° C. at 10⁻² mbar.

Figure 23:
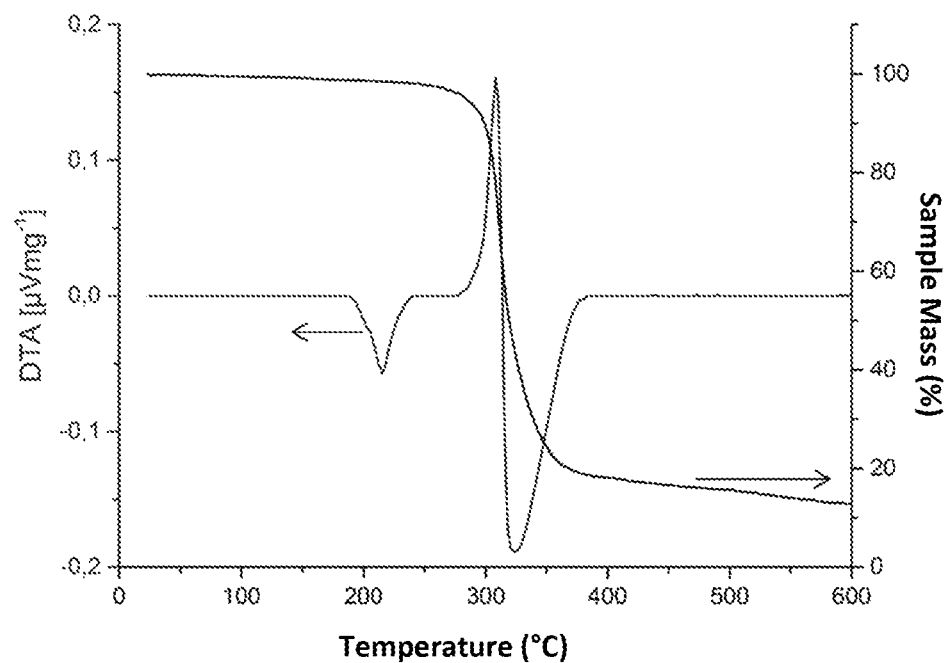
FIG. 23 is a chart showing a differential thermal analysis (DTA) and a thermogravimetry analysis for Compound C23 of Example 23.

The differential thermal analysis (DTA) and the thermogravimetry analysis of C23 are depicted in FIG. 23. The DTA shows an exothermic peak at 318° C. and two endothermic peaks at 216° C. and 326° C. respectively. Deriving from the thermogravimetry analysis, the sample has lost 87.2% of its mass at 600° C.

Example 24

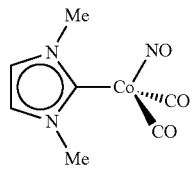

C24 scale: [Co(CO)₃(NO)] 586 mg (3.39 mmol, 76.8 mg/mL in Et₂O); Me₂Im 260 mg (2.71 mmol).

yield: 361 mg (1.49 mmol, 55%) of a ruby coloured solid.

¹H-NMR (500 MHz, C₆D₆): δ=2.89 (6 H, CH₃), 5.91 (s, 2 H, CHCH).

¹³C{¹H}-NMR (126 MHz, C₆D₆): δ=38.0 (CH₃), 122.2 (CHCH).

The metal-bound carbene and carbonyl carbons were not detected.

CHN for [Co(IMe)(CO)₂(NO)] [C₇H₈CoN₃O₃] [241.09 g/mol] calcd. (found): C, 34.87 (34.94); H, 3.34 (3.21); N, 17.43 (17.40).

Sublimation: 25° C. at 10⁻² mbar.

Figure 24:
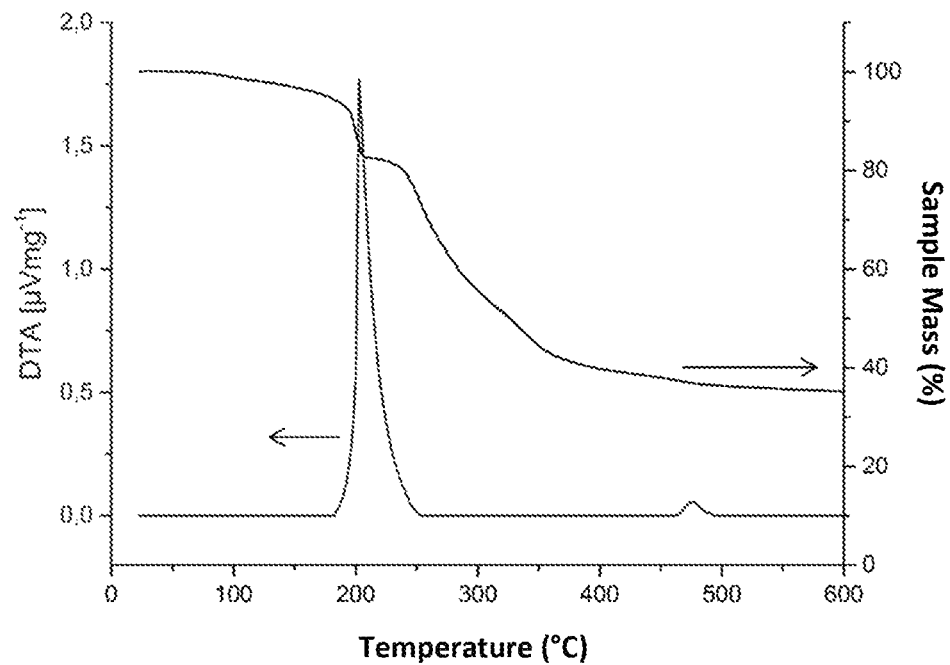
FIG. 24 is a chart showing a differential thermal analysis (DTA) and a thermogravimetry analysis for Compound C24 of Example 24.

The differential thermal analysis (DTA) and the thermogravimetry analysis of C24 are depicted in FIG. 24. The DTA shows two exothermic peaks at 203° C. and 475° C. respectively. Deriving from the thermogravimetry analysis, the sample has lost 64.8% of its mass at 600° C.

Example 25

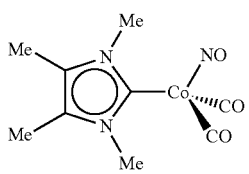

C25 scale: [Co(CO)₃(NO)] 346 mg (2.00 mmol, 76.8 mg/mL in Et₂O); Me₂(Me₂)Im 200 mg (1.60 mmol).

yield: 293 mg (1.09 mmol, 68%) of an orange coloured solid.

¹H-NMR (500 MHz, C₆D₆): δ=1.27 (s, 6 H, CCH₃), 2.90 (s, 6 H, NCH₃).

¹³C{¹H}-NMR (126 MHz, C₆D₆): δ=8.8 (CCH₃), 34.9 (NCH₃), 125.5 (CMe).

The metal-bound carbene and carbonyl carbons were not detected.

CHN for [Co($^{Me}$IMe)(CO)₂(NO)] [C₉H₁₂CoN₃O₃] [269.15 g/mol] calcd. (found): C, 40.16 (40.06); H, 4.49 (4.56); N, 15.61 (15.20).

Sublimation: 25° C. at 10⁻² mbar.

Figure 25:
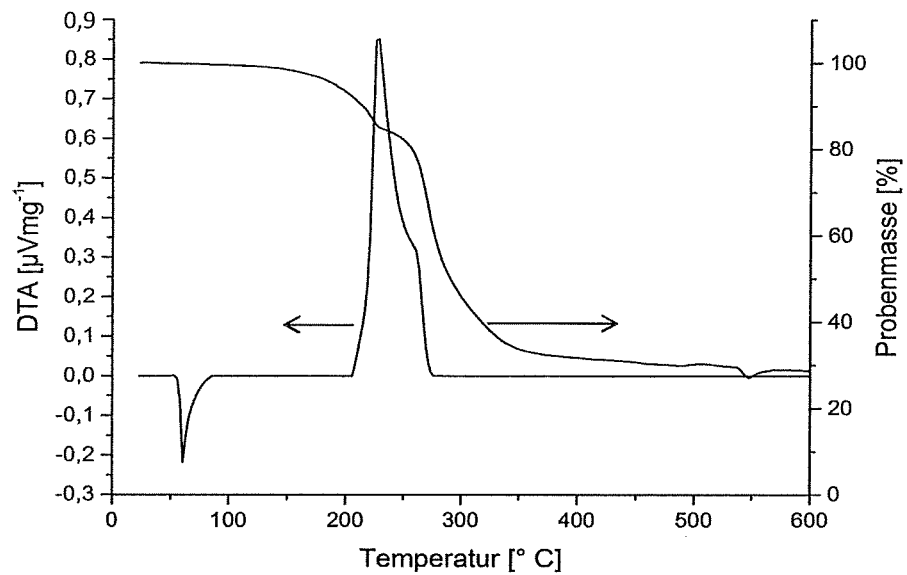
FIG. 25 is a chart showing a differential thermal analysis (DTA) and a thermogravimetry analysis for Compound C25 of Example 25.

The differential thermal analysis (DTA) and the thermogravimetry analysis of C25 are depicted in FIG. 25. The DTA shows two exothermic peaks at 228° C. and 261° C. respectively and an endothermic peak at 60° C. Deriving from the thermogravimetry analysis, the sample has lost 71.3% of its mass at 600° C.

Example 26

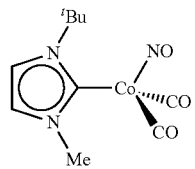

C26 scale: [Co(CO)₃(NO)] 7.77 g (44.2 mmol, added neat); Me-t-BuIm 4.81 mg (34.3 mmol).

yield: 8.61 g (30.4 mmol, 89%) of a ruby coloured solid.

¹H-NMR (500 MHz, C₆D₆): δ=1.44 (s, 9 H, C(CH₃)₃), 2.77 (s, 3 H, NCH₃), 5.91 (s, 1 H, MeNCH), 6.51 (s, 1 H, ᵗBuNCH).

¹³C{¹H}-NMR (126 MHz, C₆D₆): δ=30.2 (C(CH₃)₃), 38.7 (NCH₃), 58.2 (CMe₃), 119.0 (MeNCH), 121.0 (ᵗBuNCH).

The metal-bound carbene and carbonyl carbons were not detected.

CHN for [Co(I$^n$Pr)(CO)₂(NO)] [C₁₁H₁₅CoN₃O₃] [283.17 g/mol] calcd. (found): C, 42.42 (42.42); H, 5.98 (5.14); N, 14.84 (14.95).

Sublimation: 25° C. at 10⁻² mbar.

Figure 26:
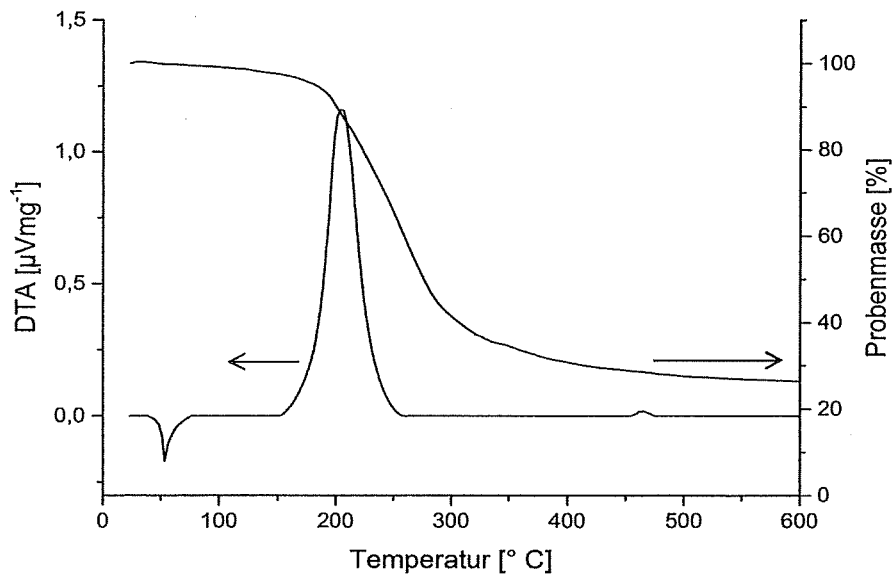
FIG. 26 is a chart showing a differential thermal analysis (DTA) and a thermogravimetry analysis for Compound C26 of Example 26.

The differential thermal analysis (DTA) and the thermogravimetry analysis of C26 are depicted in FIG. 26. The DTA shows two exothermic peaks at 204° C. and 466° C. respectively and an endothermic peak at 54° C. Deriving from the thermogravimetry analysis, the sample has lost 73.6% of its mass at 600° C.

Example 27

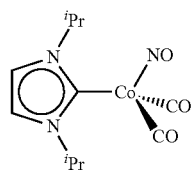

C27 scale: [Co(CO)₃(NO)] 3.27 g (18.9 mmol, added neat); i-Pr₂Im 2.60 g (17.1 mmol, 2.60 mL).

yield: 3.39 g (11.4 mmol, 82%, in two fractions) of a ruby coloured solid.

$^1$H-NMR (500 MHz, C₆D₆): δ=0.92 (d, 12 H, CH₃, $^3J_{HH}$=6.8 Hz), 4.60 (sept, 2 H, CHMe₂, $^3J_{HH}$=6.8 Hz), 6.40 (s, 2 H, CHCH).

$^{13}$C{$^1$H}-NMR (126 MHz, C₆D₆): δ=22.9 (CH₃), 52.2 (CHMe₂), 117.7 (CHCH), 186.4 (br, NCN), 219.8 (br, CO).

CHN for [Co(I$^i$Pr)(CO)₂(NO)] [C₁₁H₁₅CoN₃O₃] [297.20 g/mol] calcd. (found): C, 44.46 (44.55); H, 5.43 (5.42); N, 14.14 (14.33).

Sublimation: 35° C. at 10⁻² mbar.

Figure 27:
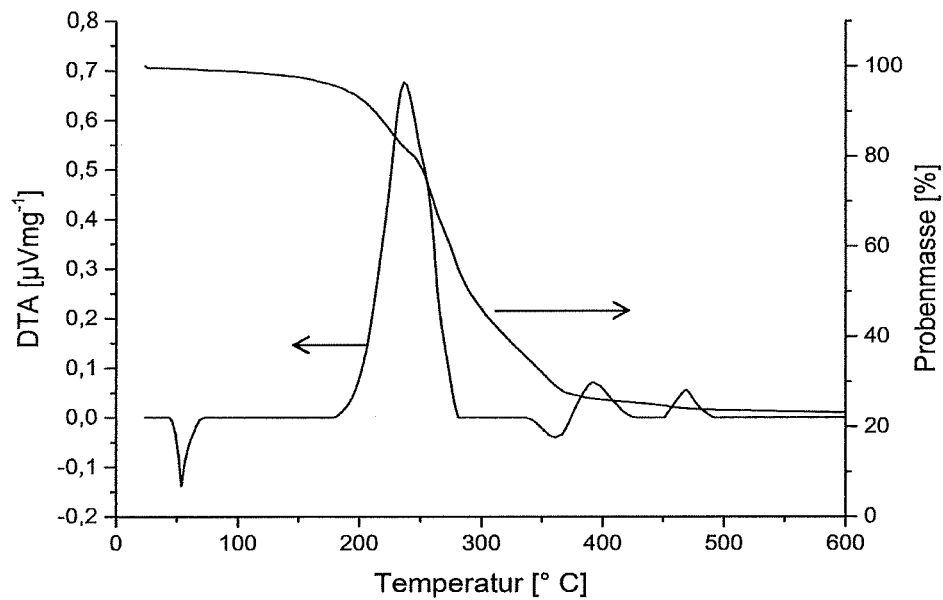
FIG. 27 is a chart showing a differential thermal analysis (DTA) and a thermogravimetry analysis for Compound C27 of Example 27.

The differential thermal analysis (DTA) and the thermogravimetry analysis of C27 are depicted in FIG. 27. The DTA shows three exothermic peaks at 236° C., 391° C. and 469° C. respectively and two endothermic peaks at 54° C. and 361° C. respectively. Deriving from the thermogravimetry analysis, the sample has lost 76.9% of its mass at 600° C.

Example 28

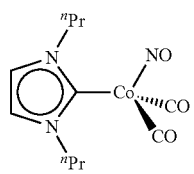

C28 scale: [Co(CO)₃(NO)] 230 mg (1.33 mmol, 76.8 mg/mL in Et₂O); i-Pr₂Im 162 mg (1.07 mmol).

product: a ruby colored oil.

$^1$H-NMR (500 MHz, C₆D₆): δ=0.63 (t, 6 H, CH₃, $^3J_{HH}$=7.4 Hz), 1.39 (qt, 4 H, CH₂Me, $^3J_{HH}$=7.4 Hz, $^3J_{HH}$=7.0 Hz), 3.48 (t, 4 H, NCH₂, $^3J_{HH}$=7.0 Hz), 6.15 (s, 2 H, CHCH).

$^{13}$C{$^1$H}-NMR (126 MHz, C₆D₆): δ=10.9 (CH₃), 24.4 (CH₂Me), 52.7 (NCH₂), 121.3 (CHCH).

The metal-bound carbene and carbonyl carbons were not detected.

CHN for [Co(I$^n$Pr)(CO)₂(NO)] [C₁₁H₁₅CoN₃O₃] [297.20 g/mol] calcd. (found): C, 44.46 (42.92); H, 5.43 (4.14); N, 14.14 (12.70).

Sublimation: 25° C. at 10⁻² mbar.

Figure 28:
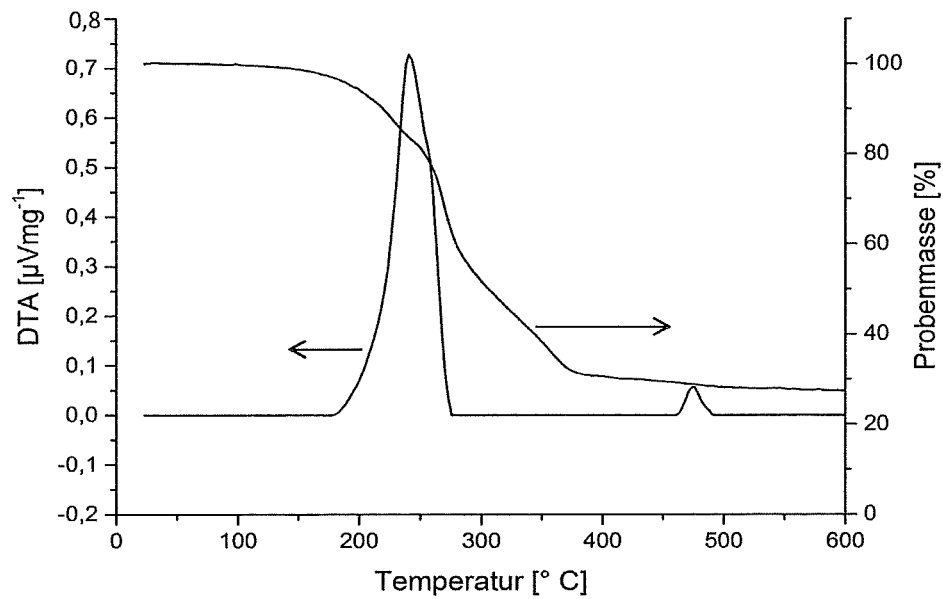
FIG. 28 is a chart showing a differential thermal analysis (DTA) and a thermogravimetry analysis for Compound C28 of Example 28.

The differential thermal analysis (DTA) and the thermogravimetry analysis of C28 are depicted in FIG. 28. The DTA shows two exothermic peaks at 241° C. and 476° C. respectively. Deriving from the thermogravimetry analysis, the sample has lost 72.6% of its mass at 600° C.

Example 29

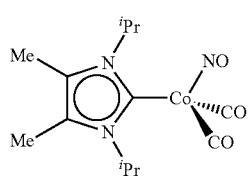

C29 scale: [Co(CO)₃(NO)] 200 mg (1.16 mmol, 50 mg/mL in Et₂O); i-Pr₂(Me₂)Im 168 mg (923 µmol).

yield: 189 mg (581 µmol, 63%) of a ruby coloured solid.

$^1$H-NMR (500 MHz, C₆D₆): δ=1.05 (d, 12 H, CH(CH₃)₂, $^3J_{HH}$=7.2 Hz), 1.65 (s, 6 H, CCH₃), 5.04 (sept, 2 H, CHMe₂, $^3J_{HH}$=7.2 Hz).

$^{13}$C{$^1$H}-NMR (126 MHz, C₆D₆): δ=10.4 (CCH₃), 21.4 (CH(CH₃)₂), 53.9 (CHMe₂), 126.7 (CMe).

The metal-bound carbene and carbonyl carbons were not detected.

CHN for [Co($^{Me}$I$^i$Pr)(CO)₂(NO)] [C₁₃H₂₀CoN₃O₃] [325.25 g/mol] calcd. (found): C, 47.84 (48.01); H, 6.20 (6.22); N, 12.92 (13.11).

Sublimation: 50° C. at 10⁻² mbar.

Figure 29:
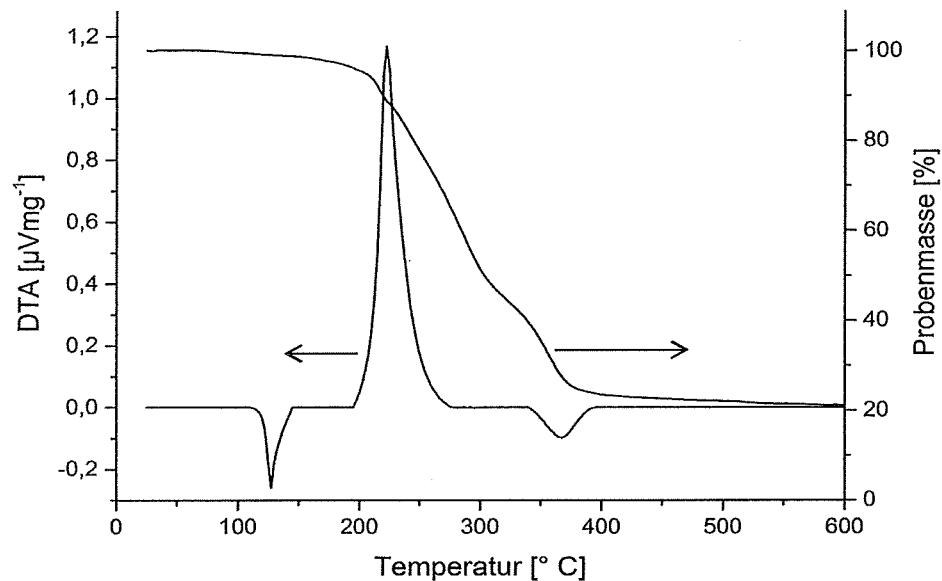
FIG. 29 is a chart showing a differential thermal analysis (DTA) and a thermogravimetry analysis for Compound C29 of Example 29.

The differential thermal analysis (DTA) and the thermogravimetry analysis of C29 are depicted in FIG. 29. The DTA shows an exothermic peak at 222° C. and two endothermic peaks at 127° C. and 367° C. respectively. Deriving from the thermogravimetry analysis, the sample has lost 78.9% of its mass at 600° C.

Example 30

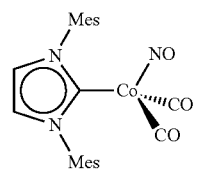

C30 scale: [Co(CO)₃(NO)] 200 mg (1.16 mmol, 50 mg/mL in Et₂O); Mes₂Im 281 mg (923 µmol).

yield: 220 mg (490 µmol, 53%) of an orange coloured solid.

$^1$H-NMR (500 MHz, C₆D₆): δ=2.00 (s, 12 H, o-CH₃), 2.10 (s, 6 H, p-CH₃), 6.27 (s, 2 H, CHCH), 6.78 (s, 4 H, m-CH$_{Ar}$).

$^{13}$C{$^1$H}-NMR (126 MHz, C₆D₆): δ=17.6 (o-CH₃), 21.1 (p-CH₃), 123.1 (CHCH), 129.5 (m-CH$_{Ar}$), 135.5 (o-C$_{Ar}$), 137.5 (i-C$_{Ar}$), 139.1 (p-C$_{Ar}$), 194.3 (br, NCN), 213.0 (br, CO).

CHN for [Co(IMes)(CO)₂(NO)] [C₂₃H₂₄CoN₃O₃] [449.11 g/mol] calcd. (found): C, 61.47 (60.98); H, 5.38 (5.65); N, 9.35 (9.61).

Sublimation: 80° C. at 10⁻² mbar.

Figure 30:
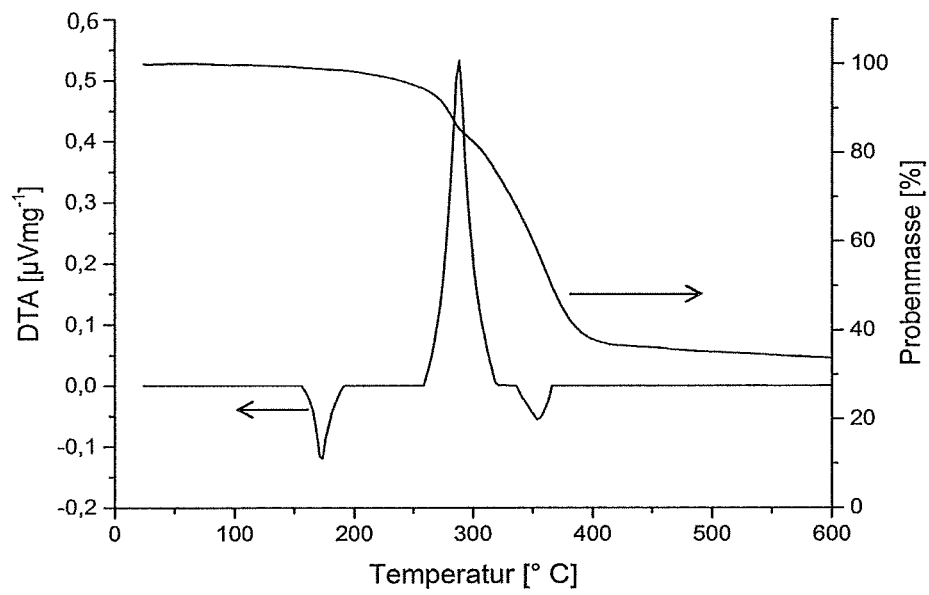
FIG. 30 is a chart showing a differential thermal analysis (DTA) and a thermogravimetry analysis for Compound C30 of Example 30.

The differential thermal analysis (DTA) and the thermogravimetry analysis of C30 are depicted in FIG. 30. The DTA shows an exothermic peak at 288° C. and two endothermic peaks at 174° C. and 354° C. respectively. Deriving from the thermogravimetry analysis, the sample has lost 66.3% of its mass at 600° C.

Example 31

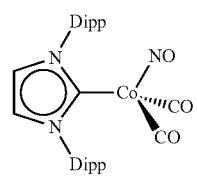

C31 scale: [Co(CO)₃(NO)] 150 mg (870 μmol, 50 mg/mL in Et₂O); Dipp₂Im 304 mg (780 μmol).

yield: 320 mg (600 μmol, 77%) of a ruby coloured solid.

¹H-NMR (500 MHz, C₆D₆): δ=1.04 (d, 12 H, CH₃, ³J$_{HH}$=6.9 Hz), 1.35 (d, 12 H, CH₃, ³J$_{HH}$=6.9 Hz), 2.70 (sept, 4 H, CHMe₂, ³J$_{HH}$=6.9 Hz), 6.66 (s, 2 H, CHCH), 7.13 (m, 4 H, m-CH$_{Ar}$), 7.25 (m, 2 H, p-CH$_{Ar}$).

¹³C{¹H}-NMR (126 MHz, C₆D₆): δ=22.8 (CH₃), 25.6 (CH₃), 28.9 (CHMe₂), 124.3 (m-CH$_{Ar}$), 124.6 (CHCH), 130,4 (p-CH$_{Ar}$), 137.4 (i-Car), 146.1 (o-C$_{Ar}$), 197.5 (br, NCN).

The metal-bound carbonyl carbon was not detected.

CHN for [Co(IPr)(CO)₂(NO)] [C₂₉H₃₆CoN₃O₃] [533.56 g/mol] calcd. (found): C, 65.28 (64.85); H, 6.85 (6.70); N, 7.88 (7.75).

IR: (ATR): û [cm⁻¹]=735 (w), 753 (w), 798 (m), 944 (w), 1017 (w), 1060 (w), 1079 (w), 1260 (w), 1322 (w), 1363 (vw), 1386 (w), 1400 (w), 1446 (w), 1467 (w), 1722 (vs, ν$_{—N=O, str.}$), 1945 (vs, ν$_{—C=O, str., (b1)}$), 2010 (vs, ν$_{—C=O, str. (A1)}$), 2870 (w, ν$_{—C—H, str.}$), 2966 (m, aryl-ν$_{—C—H, str.}$).

Sublimation: 80° C. at 10⁻² mbar.

Figure 31:
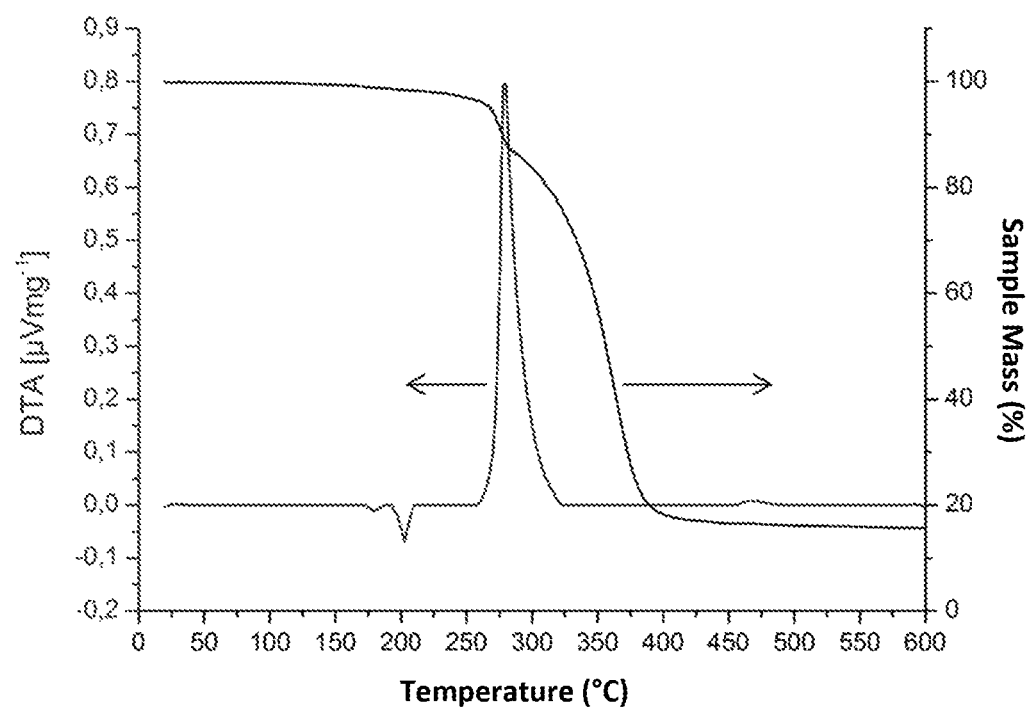
FIG. 31 is a chart showing a differential thermal analysis (DTA) and a thermogravimetry analysis for Compound C31 of Example 31.

The differential thermal analysis (DTA) and the thermogravimetry analysis of C31 are depicted in FIG. 31. The DTA shows two exothermic peaks at 280° C. and 468° C. respectively and two endothermic peaks at 178° C. and 203° C. respectively. Deriving from the thermogravimetry analysis, the sample has lost 84.3% of its mass at 600° C.

The invention claimed is:

1. A process, comprising:
bringing a carbene compound of general formula (I) into a gaseous state or an aerosol state; and
depositing the carbene compound of the general formula (I) from the gaseous state or the aerosol state onto a solid substrate;
wherein:
the compound of the general formula (I) is:

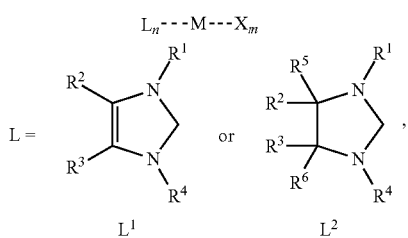

(I)

$R^1$ and $R^4$ are independent of each other an alkyl group, an aryl group or a trialkylsilyl group;
$R^2$, $R^3$, $R^5$ and $R^6$ are independent of each other hydrogen, an alkyl group or a trialkylsilyl group;
n is an integer from 1 to 3;
M is Ni or Co;
X is independently a ligand which coordinates M; and
m is an integer from 0 to 4.

2. The process according to claim 1, wherein the carbene compound of the general formula (I) is chemisorbed on a surface of the solid substrate.

3. The process according to claim 1, further comprising:
decomposing the deposited carbene compound of the general formula (I) by removal of all ligands L and X.

4. The process according to claim 3, wherein the deposited carbene compound of the general formula (I) is exposed to a reducing agent.

5. The process according to claim 3, wherein a sequence of depositing the carbene compound of the general formula (I) onto the solid substrate and decomposing the deposited carbene compound of the general formula (I) is performed at least twice.

6. The process according to claim 1, wherein $R^2$, $R^3$, $R^5$ and $R^6$ are hydrogen.

7. The process according to claim 1, wherein $R^2$ and $R^3$ are methyl.

8. The process according to claim 1, wherein n is 2.

9. The process according to claim 1, wherein $R^1$ and or $R^4$ is methyl or ten-butyl.

10. The process according to claim 1, wherein m is an integer from 2 to 4, such that one X is NO and other X are CO.

11. A method for forming a film on a solid substrate, the method comprising depositing on a carbene compound of general formula (I) on the solid substrate:

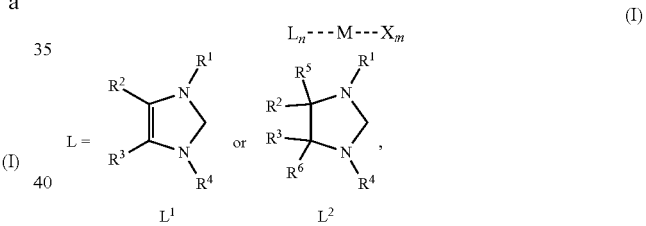

(I)

Wherein:
$R^1$ and $R^4$ are independent of each other an alkyl group, an aryl group or a triaikylsilyl group;
$R^2$, $R^3$, $R^5$ and $R^6$ are independent of each other hydrogen, an alkyl group, an aryl group or a triaikylsilyl group;
n is an integer from 1 to 3;
M is Ni or Co;
X is independently a ligand which coordinates M; and m is an integer from 0 to 4.

* * * * *

UNITED STATES PATENT AND TRADEMARK OFFICE
CERTIFICATE OF CORRECTION

PATENT NO. : 10,344,381 B2  
APPLICATION NO. : 15/325840  
DATED : July 9, 2019  
INVENTOR(S) : Julia Strautmann et al.

Page 1 of 2

It is certified that error appears in the above-identified patent and that said Letters Patent is hereby corrected as shown below:

In the Specification

Column 1, Line 35, "N-heterocylic" should read -- N-heterocyclic --,

Column 6, table, Line 23, "butyene" should read -- butylene --,

Column 6, table, Line 25, "butyene" should read -- butylene --,

Column 15, Line 43, "tBu-CH$_3$)," should read -- $^t$Bu-CH$_3$), --,

Column 15, Lines 44-45, "(s, tBuCH$_3$), 56.8 (s, tBu-C)," should read -- (s, $^t$BuCH$_3$), 56.8 (s, $^t$Bu-C), --, Column 20, Line 40, "(tBu-CH$_3$)," should read -- ($^t$Bu-CH$_3$), --, Column 20, Line 41, "(tBu-CCH$_3$)," should read -- ($^t$Bu-CCH$_3$), --, Column 20, Line 46, "tBu-CH$_3$)," should read -- $^t$Bu-CH$_3$), --, Column 20, Line 46, "tBu-CH$_3$)," should read -- $^t$Bu-CH$_3$), --, Column 20, Line 52, "(tBu-CH$_3$)," should read -- ($^t$Bu-CH$_3$), --, Column 20, Line 53, "(tBu-CH$_3$)," should read -- ($^t$Bu-CH$_3$), --, Column 20, Line 53, "(tBu-" should read -- ($^t$Bu- --, Column 21, Line 33, "[C$_{11}$H$_{15}$CoN$_5$O$_2$]" should read -- [C$_{11}$H$_{16}$CoN$_5$O$_2$] --, Signed and Sealed this  
Twenty-fourth Day of March, 2020

Andrei Iancu  
*Director of the United States Patent and Trademark Office*

CERTIFICATE OF CORRECTION (continued)

Column 21, Line 39, "$v_{-N=O, str.}$)," should read -- $v_{-N≡O, str.}$), --,

Column 21, Line 40, "$v_{-C=O, str.}$)," should read -- $v_{-C≡O, str.}$), --,

Column 22, Line 51, "tBuNCH," should read -- $^t$BuNCH, --,

Column 22, Line 54, "tBuNCH," should read -- $^t$BuNCH, --,

Column 22, Line 57, "[C17H$_{28}$CoN$_5$O$_2$]" should read -- [C$_{17}$H$_{28}$CoN$_5$O$_2$] --, Column 26, Line 44, "[C$_{11}$H$_{15}$CoN$_3$O$_3$]" should read -- [C$_{11}$H$_{16}$CoN$_3$O$_3$] --, Column 27, Line 10, "[C$_{11}$H$_{15}$CoN$_3$O$_3$]" should read -- [C$_{11}$H$_{16}$CoN$_3$O$_3$] --, Column 27, Line 45, "[C$_{11}$H$_{15}$CoN$_3$O$_3$]" should read -- [C$_{11}$H$_{16}$CoN$_3$O$_3$] --, Column 29, Line 9, "130,4" should read -- 130.4 --, Column 29, Line 9, "(i-Car)," should read -- (i-C$_{Ar}$), --, Column 29, Line 19, "$v_{-C=O, str. (A1)}$)," should read -- $v_{-C=O, str., (A1)}$), --, Column 29, Line 20, "aryl-$v_{-C-H, str.}$)." should read -- aryl-$v_{=C-H, str.}$). --, In the Claims Column 29, Lines 40-45, Claim 1, "  " should read -- ; --, Column 29, Line 53, Claim 1, "or a" should read -- an aryl group or a --, Column 30, Line 24, Claim 9, "and or" should read -- and/or --, Column 30, Line 25, Claim 9, "ten-butyl." should read -- tert-butyl. --, Column 30, Line 30, Claim 11, "on a" should read -- a --, Column 30, Line 44, Claim 11, "Wherein:" should read -- wherein: --, Column 30, Line 46, Claim 11, "triaikylsilyl" should read -- trialkylsilyl --, Column 30, Line 48, Claim 11, "triaikylsilyl" should read -- trialkylsilyl --.